US009603319B2

(12) United States Patent
Van Leeuwen et al.

(10) Patent No.: US 9,603,319 B2
(45) Date of Patent: Mar. 28, 2017

(54) **TSWV RESISTANT *CAPSICUM* PLANTS**

(71) Applicant: NUNHEMS B.V., AC Nunhem (NL)

(72) Inventors: Loes Van Leeuwen, Nonantola (IT); Ignacio Susin Arrieta, Aguadulce (ES); Samantha M. Guiderdone, Modena (IT); Massimo Turina, Turin (IT); Marina Ciuffo, Turin (IT)

(73) Assignee: NUNHEMS B.V., Nunhem (NL)

( * ) Notice: Subject to any disclaimer, the term of this patent is extended or adjusted under 35 U.S.C. 154(b) by 111 days.

(21) Appl. No.: 14/382,364

(22) PCT Filed: Mar. 1, 2013

(86) PCT No.: PCT/EP2013/054143
§ 371 (c)(1),
(2) Date: Sep. 2, 2014

(87) PCT Pub. No.: WO2013/127988
PCT Pub. Date: Sep. 6, 2013

(65) Prior Publication Data

US 2015/0216137 A1 Aug. 6, 2015

Related U.S. Application Data

(60) Provisional application No. 61/605,903, filed on Mar. 2, 2012.

(30) Foreign Application Priority Data

Mar. 2, 2012 (EP) .................................... 12157881

(51) Int. Cl.
*A01H 5/08* (2006.01)
*A01H 1/00* (2006.01)
*A01H 5/00* (2006.01)
*A01H 5/10* (2006.01)

(52) U.S. Cl.
CPC ................. *A01H 5/08* (2013.01); *A01H 1/00* (2013.01); *A01H 5/00* (2013.01); *A01H 5/10* (2013.01)

(58) Field of Classification Search
None
See application file for complete search history.

(56) References Cited

U.S. PATENT DOCUMENTS

2009/0064369 A1* 3/2009 Berke ...................... A01H 5/08 800/268
2009/0210965 A1* 8/2009 McCarthy ................ A01H 5/08 800/268

OTHER PUBLICATIONS

Yoon et al. Journal of the Korean Society of Horticultural Science 45(6): 324-329 (2004).*
Cebolla-Cornejo et al. Annals of Applied Biology 143: 143-152 (2003).*
International Search Report issued in corresponding International Application No. PCT/EP2013/054143, dated Mar. 26, 2013 (2 pages).
Margaria et al., "Evidence that the Nonstructural Protein of Tomato spotted wilt virus is the Avirulence Determinant in the Interaction with Resistant Pepper Carrying the Tsw Gene", Molecular Plant-Microbe Interactions (2007), vol. 20, No. 5, pp. 547-558.
Jahn et al., "Genetic Mapping of the Tsw Locus for Resistance to the Tospovirus Tomato spotted wilt virus in *Capsicum* spp. and Its Relationship to the Sw-5 Gene for Resistance to the Same Pathogen in Tomato", Molecular Plant-Microbe Interactions (2000), vol. 13, No. 6, pp. 673-682.
Sharman et al., "Field isolates of Tomato spotted wilt virus overcoming resistance in capsicum in Australia", Australasian Plant Pathology (2006), vol. 35, pp. 123-128.
Pappu et al., "Global status of tospovirus epidemics in diverse cropping systems: Success achieved and challenges ahead", Virus Research (2009), vol. 141, No. 2, pp. 219-236.
German et al., "Tospoviruses: Diagnosis, Molecular Biology, Phylogeny, and Vector Relationships", Annu. Rev. Phytopathol. (1992), vol. 30, pp. 315-348.
Black et al., "Tomato Spotted Wilt Virus Resistance in Capsicum chinense PI 152225 and 159236", Plant Disease (1991), vol. 75, pp. 863.
Boiteux, L.S., "Allelic relationships between genes for resistance to tomato spotted wilt tospovirus in Capsicum chinense", Theor. Appl. Genet. (1995), vol. 90, pp. 146-149.
Costa et al., "Introduction of Genetic Resistance to TSWV from C. Chinense 'PI-159236' in Different Pepper Genetic Backgrounds", ACTA Hortic. (1995), vol. 412, pp. 523-532.
Roggero et al., "Resistance to tospoviruses in pepper", Thrips and Tospoviruses: Proceedings of the 7th International Symposium on Thysanoptera (2000), pp. 105-110.
Moury et al., "A CAPS marker to assist selection of tomato spotted wilt virus (TSWV) resistance in pepper", Genome (2000), vol. 43, pp. 137-142.
Boiteux et al., "Susceptibility of Casicum chinense PI 159236 to Tomato Spotted Wilt Virus Isolates in Brazil", Plant Disease (1993), vol. 77, No. 2, p. 210.
Moury et al., "Hypersensitive resistance to tomato spotted wilt virus in three Capsicum chinense accessions is controlled by a single gene and is overcome by virulent strains", Euphytica (1997), vol. 94, pp. 45-52.
Roggero et al., "Two Field Isolates of Tomato Spotted Wilt Tospovirus Overcome the Hypersensitive Response of a Pepper (*Capsicum annuum*) Hybrid with Resistance Introgressed from C. chinense PI152225", Plant Disease (1999), vol. 83, p. 965.

(Continued)

*Primary Examiner* — David T Fox
(74) *Attorney, Agent, or Firm* — Arent Fox LLP

(57) ABSTRACT

The present invention relates to the field of pepper breeding. Provided are plants which are resistant against a Tsw-resistance breaking pathotype of TSWV. Also provided are plant parts, seeds, cells and fruits thereof and methods to produce such plants.

19 Claims, 2 Drawing Sheets

(56) References Cited

OTHER PUBLICATIONS

Figure 2:
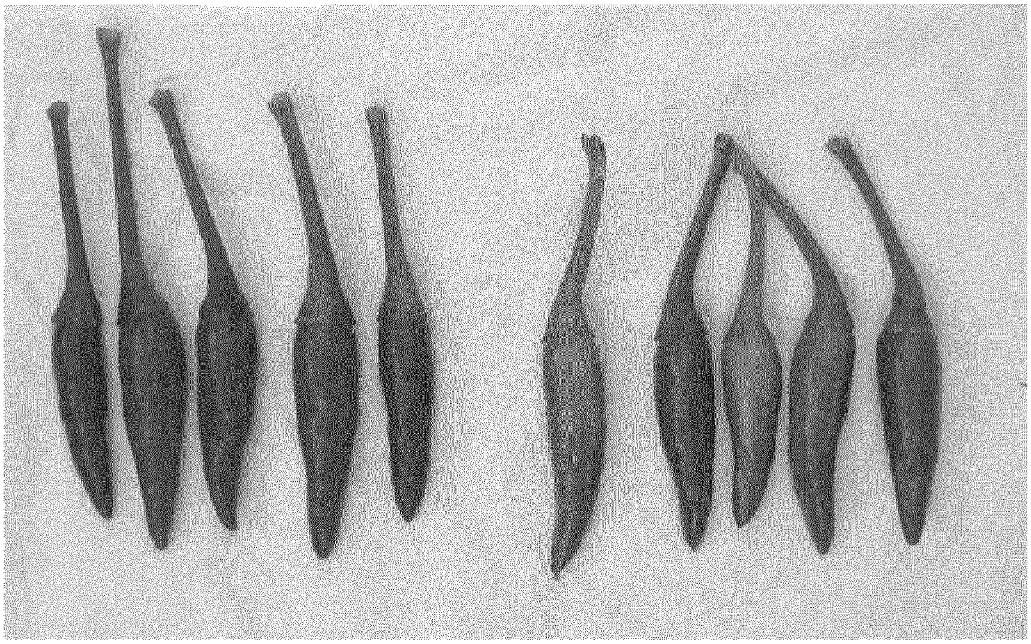

Roggero et al., "Field Isolates of Tomato spotted wilt virus Overcoming Resistance in Pepper and Their Spread to Other Hosts in Italy", Plant Disease (2002), vol. 86, No. 9, pp. 950-954.
Margaria et al., "Resistance breaking strain of Tomato spotted wilt virus (Tospovirus; Bunyaviridae) on resistant pepper cultivars in Almeria, Spain", Plant Pathology (2004), vol. 53, p. 795.

* cited by examiner

Figure 1 a) - NSs protein of $Ve430^{RB}$

```
        10         20         30         40         50         60
MMSSSVYESI IQTRASVWGS TASGKAVVDS YWIHELGTGS QLVQTQLYSD SRSKSSFGYT

        70         80         90        100        110        120
AKVGDLPCEE EEILSQHVYI PIFDDIDFSI NIDDSVLALS VCSNTVNANG VKHQGHLKVL

       130        140        150        160        170        180
SPAQLHSIGS IMNRSDITDR FQLQEKDIIP NDRYIEAANK GSLSCVKEHT YKIEMCYNQA

       190        200        210        220        230        240
LGKVNVLSPN RNVHEWLYSF KPNFNQVESN NRTVNSLAVK SLLMSAENNI MPNSQAFVKA

       250        260        270        280        290        300
STDSHFKLSL WLRVPKVLKQ ISIQKLFKVA GDETNKTFYL SIACIPNHNS VETALNITVI

       310        320        330        340        350        360
CKHQLPIRKC KAPFELSMMF SDLKEPYNIV HDPSYPQRIV HALLETHTSF AQVLCNNLQE

       370        380        390        400        410        420
DVIIYTLNNH ELTSGKLDLG ERTLNYSEDA YKRKYFLSKT LECLPSNTQT MSYLDSIQIP

       430        440        450        460
SWKIDFARGE IKISPQSISV AKSLLKLDLS GIKKKESKIK EAYASGSK
```

Figure 1 b) - NSs protein of $Ve427^{wt}$

```
        10         20         30         40         50         60
MMSSSVYESI IQTRASVWGS TASGKAVVDS YWIHELGTGS QLVQTQLYSD SRSKSSFGYT

        70         80         90        100        110        120
AKVGDLPCEE EEILSQHVYI PIFDNIDFSI NIDDSVLALS VCSNTVNANG VKHQGHLKVL

       130        140        150        160        170        180
SPAQLHSIGS IMNRSDITDR FQLQEKDIIP NDRYIEAANK GSLSCVKEHT YKIEMCYNQA

       190        200        210        220        230        240
LGKVNVLSPN RNVHEWLYSF KPNFNQVESN NRTVNSLAVK SLLMSAENNI MPNSQAFVKA

       250        260        270        280        290        300
STDSHFKLSL WLRVPKVLKQ ISIQKLFKVA GDETNKTFYL SIACIPNHNS VETALNITVI

       310        320        330        340        350        360
CKHQLPIRKC KAPFELSMMF SDLKEPYNIV HDPSYPQRIV HALLETHTSF AQVLCNNLQE

       370        380        390        400        410        420
DVIIYTLNNH ELTSGKLDLG ERTLNYSEDA YKRKYFLSKT LECLPSNIQT MSYLDSIQIP

       430        440        450        460
SWKIDFARGE IKISPQSISV AKSLLKLDLS GIKKKESKIK EAYASGSK
```

TSWV RESISTANT *CAPSICUM* PLANTS

CROSS-REFERENCE TO RELATED APPLICATIONS

This application is the U.S. National Phase of International Patent Application No. PCT/EP2013/054143, filed Mar. 1, 2013, which claims the benefit of priority to European Application No. 12157881.9, filed Mar. 2, 2012 and U.S. Provisional Application No. 61/605,903, filed Mar. 2, 2012, the contents of each are hereby incorporated by reference in their entireties.

FIELD OF THE INVENTION

The invention relates to plant breeding and plant improvement, in particular plants of the species *Capsicum annuum* L. which are resistant against Tsw-resistance breaking strain Ve427$^{RB}$.

BACKGROUND OF THE INVENTION

*Capsicum annuum* L. plants are herbaceous plants of the family Solanaceae. The plant reaches about 0.5-1.5 meters (20-60 in). Single white flowers bear the pepper fruit which is green when unripe, changing principally to red, although some varieties may ripen to brown or purple. While the species can tolerate most climates, they are especially productive in warm and dry climates. Cultivated pepper plants of the species *Capsicum annuum* include different types of peppers, such as bell peppers, cayenne peppers, paprika, and jalapeños.

Tospoviruses are an important pathological threat to many plant species, causing considerable damage and yield loss worldwide (German et al. 1992, Ann Rev Phytopath V30: 315-348). Genes conferring or enhancing tospovirus resistance are therefore continuously sought after by plant breeders in order to develop resistant cultivars. The Sw-5 gene was transferred from *Lycopersicon peruvianum* into cultivated tomato, conferring resistance to Tospovirus serogroup I (e.g. TSWV, Tomato Spotted Wilt Virus) and serogroup II (e.g. GRSV and TCSV, Groundnut Ringspot Virus and Tomato Cholrotic Spot Virus, respectively).

Commercial sweet and hot pepper cultivars nowadays frequently contain the dominant resistance gene Tsw, which confers hypersensitive resistance to TSWV (but not to other Tospoviruses, such as GRSV or TCSV). The Tsw gene has been introgressed from lines of the species *Capsicum chinense*, PI152225, PI159236 (Black et al. 1991, Plant Disease 75: 863; Boiteux et al 1995, Theor. Appl. Genet. 90: 146-149; Costa et al. 1995, First Int. Symposium on Solanaceae for the Fresh Market, Mar. 28-31 1995, Malaga, Spain, Acta Hortic. 412: 523-532). Molecular markers for identifying and/or selecting Tsw have also been developed (Moury et al. 2000, Genome 43: 137-142) and Jahn et al. (2000, MPMI Vol 13: 673-682) have mapped the Tsw gene to chromosome 10 in *Capsicum annuum*.

One drawback is that the TSWV resistance conferred by the Tsw gene is broken by high temperatures and also depends on plant age (young plants are more susceptible). Scientific evidence seems to suggest that the Tsw-resistance gene may work by impairing the long-distance transport of TSWV (see Rogero et al, Thrips and Tospoviruses: Proceedings of the 7$^{th}$ Int Symposium on Thysanoptera, pp 105-110).

An additional problem of the Tsw gene is that Tsw-resistance breaking strains of TSWV have been reported.

The Tsw-resistance breaking strains are able to systemically infect plants carrying the dominant Tsw resistance gene. The first report of a resistance breaking strain, breaking the resistance of *C. chinense*, was in 1993 (Boiteaux et al. Plant Disease 77: 210). Later Moury et al. (1997, Euphytica 1994: 45-52) also found viral strains overcoming the Tsw resistance, although the virus isolates were not typed to assess if they were indeed TSWV isolates, rather than GRSV or TCSV isolates.

Roggero et al. (1999, Plant Disease Vol 83: p 965) found two field isolates of TSWV in Italy which overcame the Tsw-resistance in a pepper hybrid carrying the Tsw gene from PI15225. Serological assays confirmed that the virus isolates were TSWV strains, which were transmissible by the thrips vector *Frankliniella occidentalis*. In 2002 Roggero et al. reported further Tsw-resistance breaking strains in Italy (Plant Disease Vol 86: 950-954). All of the commercial pepper cultivars tested could be systemically infected by these resistance-breaking TSWV strains under experimental conditions. However, TSWV resistant tomato cultivars, carrying the Sw-5 gene, were not susceptible to Tsw-resistance breaking strains from pepper, showing that Sw-5 and Tsw have different characteristics (Roggero et al. 2002, supra). This was also confirmed by Jahn et al. (2000, supra).

In 2004, Margaria et al. (Plant Pathology Vol 53: p 794) reported the identification of Tsw-resistance breaking strains in the field in Spain (Almeria).

Margaria et al. 2007 (MPMI Vol 20: 547-558) studied the interaction between pepper plants carrying the dominant Tsw resistance gene and various natural TSWV strains, both wild type strains and strains which were able to break Tsw-resistance. Tsw-resistance breaking TSWV strains are designated by the superscript 'RB' in their study. One of these resistance breaking strains is Ve427$^{RB}$ isolated in 2003 from a pepper field in Almeria, Spain. In contrast to the wild type TSWV strains which caused only local damages on the inoculated pepper leaves of plants carrying the Tsw-gene, resistance breaking TSWV strains caused systemic infections, leading to, e.g., leaf chlorosis and yellow mottle throughout the infected plants. By using strains with reassortments between wild type (strain Br01$^{wt}$) and RB strain genomes, Margaria et al. (2007, MPMI Vol 20: 547-558) were able to show that the avirulance determinant of the Tsw-resistance breaking strains is the NSs protein (nonstructural protein) found on the small RNA (S RNA). In resistance-breaking strains of this study, the NSs protein contained one or two mutations or deletions relative to the wild type NSs protein.

Although the dominant Tsw gene is still useful in providing resistance against TSWV to pepper varieties in many parts of the world, new sources of TSWV resistance are urgently needed, in order to minimize damage caused by new TSWV strains, especially by Tsw-resistance breaking strains.

It is an object of the invention to provide pepper plants comprising a new resistance gene, different from the Tsw-gene, which confers resistance against Tsw-resistance breaking strains, such as strains comprising mutations and/or deletions in the NSs protein. In one embodiment, the new resistance gene confers at least resistance against Tsw-resistance breaking strain Ve427$^{RB}$. It is a further object of the invention to provide pepper plants comprising both the new resistance gene and the Tsw gene, i.e. plants which are resistant against wild type TSWV strains (pathotype P0) and against Tsw-resistance breaking strains (pathotype P1), at least against Ve427$^{RB}$, but preferably also against other Tsw-resistance breaking strains (such as strains having one or more deletions and/or mutations in the NSs protein and/or strains which are capable of systemic infection of pepper plants carrying the Tsw-gene).

DETAILED DESCRIPTION OF THE INVENTION

As used herein, the term "to comprise" and its conjugations is used in its non-limiting sense to mean that items following the word are included, but items not specifically mentioned are not excluded. Nevertheless, the skilled person will understand that the teen "comprise" also encompasses the tei in "consists". Thus, in embodiments of the present invention, an element that comprises a sub-element, e.g. a QTL, may also consists of said sub-element. In addition, reference to an element by the recitation of "a" or "an" does not exclude the possibility that more than one of the element is present, unless the context clearly requires that there be one and only one of the elements. Thus, "a" or "an" usually means "at least one" or "one or more", e.g., "a cell" refers also to several cells in the form of cell cultures, tissues, whole organism, etc. Similarly, "a plant" also refers to a plurality of plants.

"Phenotype" is the observable external and/or physiological appearance of the plant as a result of the interaction between its genotype and its environment. It includes observable morphological and/or physiological characteristics.

"Genotype" is the total of inheritable genetic information of a plant, partly influenced by the environmental factors, which is expressed in the phenotype.

As used herein, "pepper plant" or "pepper" is a plant of genus *Capsicum* or parts thereof (e.g. fruits). Pepper includes all kinds of peppers, such as hot/pungent peppers and non-pungent peppers (sweet pepper). The term encompasses wild accessions and domesticated peppers.

"Domesticated pepper" refers to the species *Capsicum annuum* L., *Capsicum chinense* Jacq., *Capsicum frutescens* L., *Capsicum baccatum* L., and *Capsicum pubescens* Ruiz & Pay.

The term "cultivar" (or "cultivated" plant) is used herein to denote a plant having a biological status other than a "wild" status, which "wild" status indicates the original non-cultivated, non-domesticated, or natural state of a plant or accession, and the term cultivated does not include such wild, or weedy plants. The term cultivar does include material with good agronomic characteristics, such as breeding material, research material, breeding lines, elite breeding lines, synthetic population, hybrid, founder stock/base population, inbred lines, cultivars (open pollinated of hybrid cultivar), segregating population, mutant/genetic stock, and advanced/improved cultivar. In one embodiment the term cultivar also includes landraces, i.e. pepper plants (or populations) selected and cultivated locally by humans over many years and adapted to a specific geographic environment and sharing a common gene pool. In general, "cultivated pepper" refers to breeding lines and varieties of domesticated pepper, which is cultivated by humans in the field or in protected environments (e.g. greenhouse or tunnels) for fruit production. Cultivars have good agronomic properties compared to wild accessions such as high yielding, bigger fruit size, higher fertility, higher uniformity of plants and/or fruits, etc. Examples of cultivars include cultivated varieties that belong to the species *Capsicum annuum, Capsicum* chinense, *Capsicum frutescens, Capsicum baccatum* and *Capsicum pubescens.*

As used herein, the term "plant" includes the whole plant or any parts or derivatives thereof, such as plant organs (e.g., harvested or non-harvested fruits, leaves, seed, flowers, etc.), plant cells, plant protoplasts, plant cell or tissue cultures from which whole plants can be regenerated, plant calli, plant cell clumps, and plant cells that are intact in plants, or parts of plants, such as embryos, pollen, ovules, ovaries, fruits (e.g., harvested tissues or organs, such as harvested pepper fruits or parts thereof), flowers, leaves, seeds, clonally propagated plants, roots, root-stocks, stems, root tips and the like. Also any developmental stage is included, such as seedlings, immature and mature, etc.

The term "fruit" as used herein refers to pepper fruits which were growing on a pepper plant which confers resistance against Tsw-resistance breaking strains such as strain $Ve427^{RB}$. In one embodiment, a fruit is a harvested fruit. In one embodiment, such a fruit is seedless, i.e., it contains no seeds at all, or it contains non-viable seeds, or it does not contain mature seeds in all phases of its development including mature phase, i.e., they are not suitable for propagation via seeds.

The terms "pulp", "pod" or "flesh" of a pepper fruit refers to the parts of a fruit which are not seeds. In general, fruit pulp encapsulates seeds, i.e., pulp and seeds form a fruit in the meaning of the present invention.

"Plant variety" is a group of plants within the same botanical taxon of the lowest grade known, which (irrespective of whether the conditions for the recognition of plant breeder's rights are fulfilled or not) can be defined on the basis of the expression of characteristics that result from a certain genotype or a combination of genotypes, can be distinguished from any other group of plants by the expression of at least one of those characteristics, and can be regarded as an entity, because it can be multiplied without any change. Therefore, the term "plant variety" cannot be used to denote a group of plants, even if they are of the same kind, if they are all characterized by the presence of one locus or gene (or a series of phenotypical characteristics due to this single locus or gene), but which can otherwise differ from one another enormously as regards the other loci or genes.

A "plant line" or "breeding line" refers to a plant and its progeny. As used herein, the term "inbred line" refers to a plant line which has been repeatedly selfed.

"$F_1$, $F_2$, etc." refers to the consecutive related generations following a cross between two parent plants or parent lines. The plants grown from the seeds produced by crossing two plants or lines is called the $F_1$ generation. Selfing the $F_1$ plants results in the $F_2$ generation, etc. "$F_1$ hybrid" plant (or $F_1$ hybrid seed) is the generation obtained from crossing two inbred parent lines.

"Hybrid" or "hybrid plant" is a plant produced by the intercrossing (cross-fertilization) of at least two different plants or plants of different parent lines. It is understood that the seeds of such a cross (hybrid seeds) are encompassed herein, as well as the hybrid plants grown from those seeds and plant parts derived from those grown plants.

The term "trait" refers to a heritable characteristic, such as TSWV resistance, which is transferable, e.g., by crossing and selection from one plant to another.

"TSWV", "TSWV strains" or "TSWV isolates" or "TSWV pathotypes" refers to strains of Tomato Spotted Wilt Virus which can be determined serologically (using e.g. antibodies raised against the TSWV nucleocapsid or glycoprotein, see Roggero and Masenga, 2002, Plant Dis. Vol 86, 950-953) or by sequence comparison, e.g. by comparing a strain to Brazilian isolate $Br01^{wt}$ for which the complete genome sequence has been determined (GenBank Accession numbers NC_002050, NC_002051 and NC_002052).

"Wild Type (WT) TSWV strains" or "pathotype P0" refers to TSWV strains to which the dominant Tsw-resistance gene known from the art confers resistance. For example, a resistant plant having the Tsw-resistance gene does essentially not show systemic symptoms such as yellow mottling on upper, non-inoculated leaves following infection or following artificial inoculation as for example can be done in a resistance assay using pathotype P0 as described herein. Examples of WT TSWV strains are e.g. p $105^{WT}$ or $Ve430^{WT}$ which are both described in Margaria et al. (2007, MPMI Vol 20: 547-558). Both strains can be identified by their S segment sequences which are deposited in the GenBank under accession No.: DQ376178 and DQ376184, respectively.

A "TSWV resistance gene" or a "TSWV resistance allele" is a gene or allele or DNA region comprising said gene or allele which, when present in the plant genome, confers or enhances resistance against one or more strains of TSWV compared to a plant lacking the gene or allele or DNA region.

"Tsw gene" or "Tsw resistance gene" refers to the dominant resistance gene as known in the art, e.g., obtainable from *C. chinense* PI152225, PI159236 or from commercial pepper varieties comprising the Tsw gene, such as *C. annuum* cv. Explorer (a commercial hybrid bell pepper variety). The presence or absence of the Tsw gene can be determined using a resistance assays as described in the Examples and/or using a molecular marker assay provided in the prior art (e.g. Moury et al. 2000, Genome 43: 137-142 and Jahn et al. 2000, MPMI Vol 13: 673-682).

"Tsw-resistance breaking strain" (RB) or "pathotype P1" refers to TSWV strains capable of causing systemic disease symptoms (yellow mottle on upper, non-inoculated leaves) on plants comprising a functional Tsw-resistance gene, such as e.g. on plants of *C. chinense* PI152225, PI159236 or *C. annuum* cultivar "Explorer". In one embodiment, local necrotic lesions are formed on the inoculated leaf. In one embodiment, the Tsw-resistance breaking strains comprise one or more mutations and/or deletions in the nonstructural protein (NSs) (see Margaria et al. (2007, MPMI Vol 20: 547-558) and de Haan et al. (1990, J. Gen. Virol. 71: 1001-1007)).

"$Ve427^{RB}$" refers to the RB-strain isolated from a field in Spain (Almeria) as described in Margaria et al. (2004, 2007, supra) and of which a representative sample has been deposited at the DSZM under Accession number DSM 24829.

A pepper plant having or comprising "$Ve427^{RB}$-resistance" or being "$Ve427^{RB}$-resistant" refers to a pepper plant which does not develop systemic symptoms after inoculation or infection with $Ve427^{RB}$. This can be tested using various methods, one example is using an artificial inoculation assay, such as for example the $Ve427^{RB}$-resistance assay as described herein, whereby, for example, the two youngest leaves of a pepper plant having five to six fully developed leaves, are inoculated with $Ve427^{RB}$, and the upper, non-inoculated leaves do not show yellow mottle symptoms at about 28 days after inoculation. In one embodiment a plant line or variety is said to be resistant towards $Ve427^{RB}$ if it shows essentially no systemic symptoms, meaning that at least 60% of infected or inoculated plants, preferably at least 70%, 75%, 80%, 85%, 90% or more (e.g. 92%, 93%, 94%, 95%, 98%, 99% or 100%) show no systemic symptoms (i.e. no yellow motteling on upper, non-inoculated leaves).

A "genetic element which genetic element comprises a $Ve427^{RB}$-resistance conferring QTL or a $Ve427^{RB}$ resistance conferring part thereof" or a "$Ve427^{RB}$ resistance-conferring QTL" refers to a genetic element, e.g., a nucleic acid (such as genomic DNA), which confers or enhances in a pepper plant resistance against Tsw-resistance breaking strain $Ve427^{RB}$. In one embodiment said genetic element is derivable from/obtainable from a *Capsicum* plant of wild accession PA2638. So, in one embodiment the genetic element can be obtained (is obtainable) by crossing a plant of accession PA2638 with another pepper plant. "Wild accession PA2638" as used herein refers to a wild accession obtained from a market in Italy. A representative sample of seeds of PA2638 has been deposited by Nunhems B.V. on 23 Feb. 2012 under accession number NCIMB 41936. In one embodiment the presence or absence of the genetic element which comprises a $Ve427^{RB}$ resistance-conferring QTL in a plant can be determined using a resistance assay, for example the assay described herein as "$Ve427^{RB}$-resistance assay" and/or a molecular markers assay. In one embodiment, the genetic element which comprises a $Ve427^{RB}$ resistance conferring QTL originates, is obtained from, is obtainable from, is derived from, is derivable from is found in seeds deposited under Accession number NCIMB 41817, NCIMB 41818 or NCIMB 41936, and plants grown from these seeds and/or progeny thereof. Thus, in one embodiment the genetic element which comprises a $Ve427^{RB}$ resistance conferring QTL originates, is obtained from, is obtainable from, is derived from, is derivable from crossing a plant of which seeds were deposited under Accession number NCIMB 41817, NCIMB 41818 or NCIMB 41936, with another pepper plant.

The "$Ve427^{RB}$-resistance assay" is an assay suitable to determine resistance of a pepper plant against Tsw-resistance breaking strains and/or the presence of a genetic element which comprises a $Ve427^{RB}$ resistance conferring QTL. The assay is exemplarily described further below. Using such an assay, a plant, plant line or variety can be classified as being "resistant" against a Tsw-resistance breaking strain, such as $Ve427^{RB}$.

"Resistance" refers to a statistically significant restriction in growth and/or development of a specific pathogen (e.g. one or more TSWV strains) and/or a statistically significant reduction in disease symptoms following infection with a specific pathogen (e.g. one or more TSWV strains) in plants comprising an effective (or functional) resistance gene relative to plants lacking an effective (or functional) resistance gene. Resistance may be determined qualitatively (classifying plants of a particular line or variety as 'resistant' or 'susceptible') and/or resistance may be quantified, for example in resistance assays, by e.g. measured as percentage of plants of a particular line or variety surviving infection with a virus strain (% survival) or showing essentially no systemic symptoms if only part of a plant is infected. In one embodiment a plant line or variety is said to be resistant towards a Tsw-resistance breaking strain if it is qualified as 'resistant' according to the symptoms, especially the systemic symptoms, that do not develop following infection or inoculation with the Tsw-resistance breaking strain, which can be tested in a TSWV resistance assay, e.g. as described herein. In one embodiment a plant line or variety is said to be resistant towards a Tsw-resistance breaking strain if the plant line or variety shows essentially no systemic symptoms, i.e. if at least 60% of plants, preferably at least 70%, 75%, 80%, 85%, 90% or more (e.g. 92%, 93%, 94%, 95%, 98%, 99% or 100%) show no systemic symptoms (i.e. no yellow motteling on upper, non-inoculated leaves) following infection or inoculation with the Tsw-resistance breaking strain. The skilled person will understand that at least 10 plants, 12, 15 or 20 or even more plants per line or variety should be tested under the same test conditions to evaluate whether a line or variety is resistant and that suitable control plants should be included.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species, such as pepper, may comprise a large number of different alleles at a particular locus. These may be identical alleles of the gene (homozygous) or two different alleles (heterozygous).

"Planting" or "planted" refers to seeding (direct sowing) or transplanting seedlings (plantlets) into a field by machine or hand.

"Vegetative propagation" refers to propagation of plants from vegetative tissue, e.g. by in vitro propagation. In vitro propagation involves in vitro cell culture or tissue culture and regeneration of a whole plant from the in vitro culture. Clones (i.e. genetically identical vegetative propagations) of the original plant can thus generated by in vitro culture and regeneration methods.

The term "locus" (loci plural) means a specific place or places or a site or region on a chromosome where for example a gene or a QTL or molecular marker is found. Distances between loci on the same chromosome are measured by frequency of crossing-over. The further apart two loci are, the more likely that a crossover will occur between them. Conversely, if two loci are close together, a crossover is less likely to occur between them. As a rule, one centimorgan (cM) is equal to 1% recombination between loci (e.g. markers).

The terms "QTL" and "Quantitative Trait Locus" is used herein in its art-recognised meaning. The terms refer to a region located on a particular chromosome of *Capsicum* that is associated with at least one gene (or allele) that encodes for Ve427$^{RB}$-resistance or at least a regulatory region, i.e. a region of a chromosome that controls the expression of one or more genes involved in Ve427$^{RB}$-resistance. The phenotypic expression of that gene may for instance be observed as a reduced rate of viral replication and/or as a reduced rate of viral movement through the plant and/or the phenotypic effect thereof (e.g. essentially no systemic symptoms developing). A QTL may for instance comprise one or more genes of which the products confer the genetic resistance. Alternatively, a QTL may for instance comprise regulatory genes or sequences of which the products influence the expression of genes on other loci in the genome of the plant thereby conferring the Ve427$^{RB}$-resistance.

The term "natural genetic background" is used herein to indicate the original genetic background of a QTL, i.e. the genome and chromosome where the QTL is found originally. Thus, the genome of PA2638 (Accession number NCIMB 41963) represent the natural genetic background of the genetic element which comprises a Ve427$^{RB}$-resistance conferring QTL of the invention. Conversely, a method that involves the transfer (or introgression) of a DNA region (or introgression fragment) comprising the QTL, or a resistance-conferring part thereof, from the original genetic background of PA2638 into another genetic background (e.g. onto the chromosome of another genome) of another *Capsicum* plant or species, will result in that QTL, or said resistance-conferring part thereof, not being in its natural genetic background. As used herein, the term "linkage group" is synonymous to (the physical entity of) a chromosome.

The term "molecular marker", "genetic markers" or "DNA marker" refers herein to a polymorphic nucleic acid sequence, detected by various methods to visualize differences in nucleic acid sequences. Examples of such methods are restriction fragment length polymorphism (RFLP) markers, amplified fragment length polymorphism (AFLP) markers, single nucleotide polymorphisms (SNPs), insertions, mutations, microsatellite markers (SSRs), sequence-characterized amplified regions (SCARs), cleaved amplified polymorphic sequence (CAPS) markers or isozyme markers or combinations of the markers, which defines a specific genetic and chromosomal location. A "molecular marker linked to a QTL, or gene or locus" thus refers to markers which a physically linked to the genomic DNA region which comprises a QTL, gene or locus and which co-segregate with the DNA region comprising the QTL, gene or locus. Markers can thus also define an introgression region.

A "recombination event" refers to a meiotic crossing-over event.

The term "introgression region" or "introgressed DNA region", introgressed trait" or "introgressed gene" or "introgression fragment" refers to a chromosome segment that has been transferred from one plant genome into the genome of another plant genome, by breeding methods, such as backcrossing.

"Introgression" refers herein to the transfer of a DNA region (introgression region), which confers a particular trait or phenotype (e.g. resistance against TSWV strain VE427$^{RB}$), from one plant genome into another plant genome of the same species, or of a closely related species through interspecific hybridization. In particular, the transfer of this DNA region from a non-cultivated plant or from a wild plant (lacking good agronomic properties) into the genome of a cultivated plant (having good agronomic properties) is referred to. Thus, in one embodiment the resulting pepper plant comprises a genome of a cultivated pepper plant into which genome an introgression fragment from another plant genome, in particular from PA2638, has been introgressed. Introgression generally involves breeding steps such as one or more crossings, selfings and/or backcrosses, but may also involve marker assisted selection, phenotypic selection (e.g. resistance assays), double haploid production, embryo rescue and the like.

"Backcross" refers to a breeding method wherein the plant resulting from a cross between two parents is (back) crossed with one of the parents. The parent used in the backcross is referred to as the recurrent parent. Repeated backcrossing results in the genome becoming more and more homozygous, resembling more and more that of the recurrent parent. Backcrossing can be used to introduce a trait from a donor plant (e.g. a wild accession) into another plant (e.g. a cultivated plant or breeding line).

The term "selfing" refers to the process of self-fertilization wherein an individual is pollinated or fertilized with its own pollen. A plant that has been repeatedly "selfed" (self-fertilized).

The term "protein" refers to a polypeptide having a mode of action, size, three-dimensional structure or origin. A "wild type" protein is a fully functional protein, as present in the wild type, e.g. the wild type TSWV virus strain. A "mutant protein" is herein a protein comprising one or more mutations in the nucleic acid sequence encoding the protein leading to one or more amino acids being replaced, deleted or inserted compared to the wild type protein. A "fragment" or "portion" of a protein may thus still be referred to as a "protein". An "isolated protein" is used to refer to a protein which is no longer in its natural environment.

The "wild type NSs protein" or "wild type non-structural protein" of TSWV is the NSs protein found in the wild type strain, for example the NSs protein of the strain VE430$^{WT}$ has accession number GenBank ABD38700.1 (FIG. 1 *a*), while the NSs protein of Tsw-resistance breaking strain VE427$^{RB}$ has sequence of GenBank Accession number ABD38702.1 (FIG. 1 *b*), differing only in 1 amino acid from the wild type protein (i.e. being a "mutant NSs protein") and having 99% sequence identity to the wild type protein.

A "mutation" in a nucleic acid molecule coding for a protein is a change of one or more nucleotides compared to the wild type sequence, e.g. by replacement, deletion or insertion of one or more nucleotides. A "point mutation" is the replacement of a single nucleotide, or the insertion or deletion of a single nucleotide. A "non-sense" mutation is a (point) mutation in a nucleic acid sequence encoding a protein, whereby a codon is changed into a stop codon. A truncated protein may have reduced function or loss of function. A "mis-sense" mutation is a (point) mutation in a nucleic acid sequence encoding a protein, whereby a codon is changed to code for a different amino acid. The resulting protein may have reduced function or loss of function or an altered function.

"Sequence identity" and "sequence similarity" can be determined by alignment of two peptide or two nucleotide sequences using global or local alignment algorithms. Sequences may then be referred to as "substantially identical" or "essentially similar" when they (when optimally aligned by for example the programs GAP or BESTFIT or the Emboss program "Needle" (using default parameters, see below) share at least a certain minimal percentage of sequence identity (as defined further below). These programs use the Needleman and Wunsch global alignment algorithm to align two sequences over their entire length, maximizing the number of matches and minimises the number of gaps. Generally, the default parameters are used, with a gap creation penalty=10 and gap extension penalty=0.5 (both for nucleotide and protein alignments). For nucleotides the default scoring matrix used is nwsgapdna and for proteins the default scoring matrix is Blosum62 (Henikoff & Henikoff, 1992, PNAS 89, 915-919). Sequence alignments and scores for percentage sequence identity may for example be determined using computer programs, such as the GCG Wisconsin Package, Version 10.3, available from Accelrys Inc., 9685 Scranton Road, San Diego, Calif. 92121-3752 USA or EMBOSS (http://www.ebi.ac.uk/Tools/webservices/services/emboss). Alternatively percent similarity or identity may be determined by searching against databases such as FASTA, BLAST, etc., but hits should be retrieved and aligned pairwise to compare sequence identity.

"Average" refers herein to the arithmetic mean.

"Capsaicin" is the active component of chili peppers, which are plants belonging to the genus *Capsicum*. It is an irritant for mammals, including humans, and produces a sensation of burning. The amount of capsaicin significantly varies between different varieties of *Capsicum*, including *Capsicum annuum*:

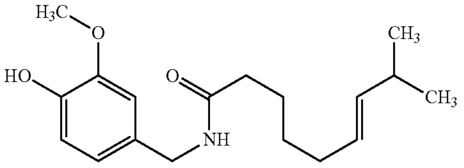

Capsaicin

The "Scoville scale" is a measurement of the spicy heat (or piquancy/pungency) of pepper. The number of Scoville heat units (SHU) indicates the amount of capsaicin present: An alcohol extract of the capsaicin oil from a measured amount of dried pepper is added incrementally to a solution of sugar in water until the "heat" is just detectable by a panel of (usually five) tasters; the degree of dilution gives its measure on the Scoville scale. Alternatively, spice heat can be measured by using high performance liquid chromatography (HPLC). This method yields results in American Spice Trade Association (ASTA) pungency units. HPLC methods are well known in the art. See, e.g., a description of DIONEX. The isocratic analytical system consisted of a pump, autosampler, thermostatic chamber, a four channel CoulArray® detector and an UV/vis detector placed before the array. LC Conditions: Column: MD-150 (3×150 mm; 3 μm), Mobile Phase: 50 mM Ammonium Acetate, pH 4.4, with acetic acid; 45% Acetonitrile, Flow Rate: 0.8 mL/min, Temperature: Ambient, Injection Volume: 20 Detectors and Conditions: Electrochemical Detector: Model 5600A, CoulArray, with Model 5010 Analytical Cell, Applied Potentials: +150, +450 mV vs. Pd, UV Detector: Standard UV detector, Wavelength: 235 and 280 nm. A measurement of one part capsaicin per million corresponds to about 15 Scoville units. However, the Scoville method is preferred when determining the piquancy/pungency of pepper.

The skilled person understands that the term "around" in combination with a value preferably refers to the exact value. However, in general, the term "around" also encompasses variations of the value due to acknowledged and accepted measuring inaccuracies within a measurement technique or within a biological distribution. In general, such an inaccuracy is below 10%, below 8%, below 6%, below 4%, below 2%, below 1%, below 0.1%, below 0.01% depending on the measurement technique. The skilled person, based on his or her general knowledge, will identify without undue burden acceptable inaccuracies within a known measurement technique or biological process such as the distribution of progenies when applying Mendel's laws.

FIGURE LEGENDS

FIG. 1 *a*: NSs protein of the strain VE430$^{WT}$ (SEQ ID NO:1).

FIG. 1 *b*: NSs protein of Tsw-resistance breaking strain VE427$^{RB}$ (SEQ ID NO:2).

FIG. 2: fruits of PA2638 (NCIMB41936). Five green fruits (right) and five red/mature fruits (left).

DETAILED DESCRIPTION OF THE INVENTION

Tsw-resistance breaking strain Ve427$^{RB}$ was, amongst other strains, found to be able to overcome resistance of pepper plants carrying the Tsw-resistance gene (Margario et al. 2004, 2007 supra). Using artificial inoculations with this strain isolated from a field in Spain, a wild *Capsicum* accession, designated PA2638, was surprisingly found which was Ve427$^{RB}$-resistant, i.e. essentially no systemic symptoms were seen when plants of PA2638 were artificially inoculated. Ve427$^{RB}$ is a strain which is capable of causing systemic infection in pepper plants comprising the Tsw-gene. Surprisingly, this new resistance source PA2638, was not resistant against the wild type TSWV strain, indicating that this new resistance source should ideally be stacked with other resistance genes, such as the dominant Tsw gene.

The wild pepper accession was confirmed by PCR analysis to lack the known Tsw-resistance gene.

The new genetic element which comprises a Ve427 resistance conferring QTL was introgressed from PA2638 into cultivated pepper by repeated backcrossing of selected, Ve427$^{RB}$-resistant $F_2$ plants. PA2638 is a hot pepper plant, i.e., the fruits of PA2638 produce/contain capsaicin. In other words, mature fruits of PA2638 contain at least 600 SHU or at least 40 ASTA pungency units.

Plant Lines

One aspect of the present invention refers to a pepper plant of the genus *Capsicum* preferably a cultivated pepper plant, which is resistant against the Tsw-resistance breaking strain of Tomato Spotted Wilt Virus (TSWV) designated Ve427$^{RB}$, a representative sample of which has been deposited under accession number DSM 24829, and said pepper plant comprises a genetic element that comprises a Ve427$^{RB}$-resistance conferring QTL or a Ve427$^{RB}$-resistance conferring part thereof which is not in its natural genetic background. For example, if the natural genetic background of said genetic element is PA2638, than a plant in accordance with the present invention is not a PA2638 plant. The plant according to the invention, thus, comprises a pepper plant having a genome of cultivated pepper, said genome comprising a Ve427$^{RB}$-resistance conferring introgression fragment from a non-cultivated pepper plant, e.g. from PA2638.

Another aspect of the present invention refers to the provision of a pepper plant of the genus *Capsicum* which comprises in its genome a genetic element derived from/obtainable from/obtained from a plant of PA2638, said genetic element comprises a Tsw-resistance-breaking TSWV-resistance conferring QTL or a Tsw-resistance-breaking TSWV resistance conferring part thereof with the proviso that the plant of the genus *Capsicum* is not PA2638.

One aspect of the present invention refers to the provision of a pepper plant of the genus *Capsicum*, which comprises in its genome a resistance conferring QTL against Tsw-resistance breaking TSWV strains which are capable of causing systemic infection in pepper plants comprising the Tsw-gene.

In one aspect, the present invention provides a pepper plant of the genus *Capsicum* which comprises in its genome a genetic element, said genetic element comprises a Tsw-resistance-breaking TSWV-resistance conferring QTL or a Tsw-resistance breaking TSWV-resistance conferring part thereof, wherein said genetic element or its resistance conferring part is not in its natural genetic background. Preferably this resistance is derived from obtained from/obtainable from PA2638, i.e., PA 2638 is the natural genetic background of said genetic element.

"Derived from", "obtained from" and "obtainable from" refer herein to a trait (and a plant comprising the trait) being obtained/obtainable by crossing a plant of which seeds were deposited under one or more accession numbers. This may involve a first cross, followed by several selfings and/or (back)crossings. Thus, the genetic element conferring the trait can be introgressed or transferred into another genetic background.

One aspect of the present invention refers to a pepper plant of the genus *Capsicum* which comprises in its genome a genetic element, said genetic element comprises a Tsw-resistance-breaking TSWV-resistance conferring QTL or a Tsw-resistance breaking TSWV-resistance conferring part thereof, which produces mature fruits having a width of at least 2 cm at its broadest width, i.e., mature fruits have a width of at least about 2 or more cm, such as at least about 3 cm, 4 cm, 5 cm, 6 cm, 7 cm, 8 cm, 9 cm, 10 cm, 11 cm, or more, and/or having a fruit length of at least 5 cm, 6 cm, 7 cm, 8 cm, 9 cm, 10 cm, 11 cm, 12 cm, 13 cm, 14 cm, 15 cm, 16 cm, 17 cm, 18 cm, 19 cm or more. For example, such a plant produces fruits of the bell type or lamuyo type.

In one embodiment, said Tsw-resistance breaking TSWV strain is characterized by a mutant NSs protein, wherein the NSs protein modification of said Tsw-resistance breaking strain is selected from one, two, three or more modifications selected from the group consisting of single amino acid exchange, deletion of an amino acid compared to the wild type protein of the related WT strain in the region where said Tsw-resistance breaking strain was isolated, rendering said Tsw-resistance breaking strain capable of overcoming resistance conferred by the dominant Tsw-gene. In one embodiment, the sequence of the NSs-protein of a wild type strain is p170$^{wt}$ as disclosed in FIG. 3 of Margaria et al. (2007, MPMI Vol 20: 547-558), p105$^{wt}$ as disclosed in FIG. 3 of Margaria et al. (2007, MPMI Vol 20: 547-558), or the sequence of the NSs-protein of Ve430$^{WT}$ having accession number ABD38700.1. In one preferred embodiment, a wild type strain of TSWV is p105$^{WT}$ or Ve430$^{WT}$, which can be identified by their S segment sequences which are deposited in the GenBank under accession No.: DQ376178 and DQ376184, respectively. In one embodiment, a Tsw-resistance breaking strain of TSWV comprises or contains one or two mutations in its NSs protein sequence selected from the group consisting of exchange of an amino acid and a deletion of an amino acid compared to the wild type NSs protein sequence, for example the NSs protein of the wild type strain having GenBank accession number ABD38700.1 and the NSs protein sequence of the Tsw-resistance breaking strain has an amino acid exchange at position 85. In one embodiment, the NSs protein of Tsw-resistance breaking strain has sequence of GenBank Accession number ABD38702.1 (referring to Ve427$^{RB}$). In one embodiment, the NSs protein of the wild type strain has GenBank accession number ABD38700.1 (see FIG. 1). In another embodiment, the NSs protein of the wild type strain is the NSs protein of p105$^{WT}$ (see accession number DQ376178).

Preferably, the Tsw-resistance breaking TSWV strain is Ve427, a representative sample of Ve427$^{RB}$ has been deposited under accession number DSM 24829. The skilled person is aware that resistance against Ve427$^{RB}$ does of course not exclude resistance against other Tsw-resistance breaking strains. However, resistance against Ve427$^{RB}$ as used herein does not include resistance against wild type strains of TSWV (i.e. strains against which the Tsw-gene confers resistance).

In one embodiment, a pepper plant according to the present invention is a pepper plant which is resistant against Tsw-resistance breaking strain Ve427$^{RB}$, wherein said pepper plant is not PA2638 (NCIMB 41936).

In one embodiment, a pepper plant having mature fruits with a length to width ratio of at most 3, preferably at most 2, and a width of 2 or more cm at its broadest width comprises a genetic element that comprises a Ve427$^{RB}$-resistance conferring QTL or a Ve427$^{RB}$-resistance conferring part thereof which is derived from/obtained from/derivable from/obtainable from wild accession, representative seeds thereof were deposited under accession number NCIMB 41936.

A pepper plant according to the present invention is preferably a cultivated pepper plant (cultivar). Moreover, the cultivated pepper plant according to the present invention may be of the species selected from the group consisting of *Capsicum annuum* (*C. annuum*), *Capsicum chinese* (*C. chinese*), *Capsicum baccatum* (*C. baccatum*), *Capsicum frutescens* (*C. frutescens*), *Capsicum pubescens* (*C. pubescens*), preferably *Capsicum annuum*. In one embodiment the pepper plant according to the present invention is an inbred line. In a specific embodiment the pepper plant according to the present invention is a hybrid, in particular an F1 hybrid. The introgression fragment comprising the Ve427$^{RB}$-resistance conferring QTL may be in heterozygous or homozygous form in the pepper plant, inbred line or F1 hybrid.

In one embodiment, a pepper plant according to the present invention is a sweet pepper plant. A "sweet pepper" in accordance with the present invention is a pepper plant of which the fruits have an average score of between 0 SHU and 500 SHU, preferably between 0 SHU and 200 SHU, more preferable between 0 SHU and 50 SHU on the Scoville scale. In one preferred embodiment, the pungency of a sweet pepper is around 0 SHU. In another embodiment, the amount of capsaicin of pepper fruits is between 0 and around 30 ASTA pungency units, preferably between 0 and 13 ASTA pungency units, or even between 0 and 2 ASTA pungency units. In different embodiments the fruits of the pepper plant according to the invention have a SHU between 0 and 100, or between 0 and 500, or between 00 and 500, or between 500 and 1000, or between 1000 and 2000, or between 2500 and 5000 or more. In further embodiments, the fruits of a pepper plant in accordance with the present invention score between around 5.000 SHU and around 20.000 SHU, or more than around 25.000 SHU, such as between 30.000 and 50.000, or between 50.000 and 100.000, or between 100.000 and 200.000, or between 100.000 and 350.000 SHU, or above 350.000 SHU.

In yet another embodiment, a pepper plant according to the invention is a pepper plant of the bell type. Generally, a bell pepper is a plant of which the mature fruits have a length/width ratio of around 1.5 to around 0.7 and an average fruit length of at least about 7.5 cm, 8 cm, 9, cm, 10 cm or more, e.g. between around 7.5 cm and around 17.5 cm. Preferably the mature fruits have a length/width ratio of around 1.3 to around 0.9 and an average fruit length of at least about 7.5 cm, 8 cm, 9, cm, 10 cm or more, e.g. a length of between around 7.5 and around 15 cm. The fruit colour can be, e.g., green, red, yellow, orange, white, rainbow (between stages of ripening) and purple. North American bell peppers refer to fruits that a about 10 cm long and about 10 cm wide, while in Europe bell peppers may be less blocky and more elongated in shape. Bell pepper is a group within the *Capsicum* genus and is of the species *Capsicum anuum* L. In one embodiment, a bell type pepper produces no capsaicin or produces only capsaicin up to 500 SHU or 30 ASTA pungency units. In one preferred embodiment, a bell pepper does not produce capsaicin. In yet another embodiment, the shape of a bell type fruit is essentially identical to the shape of bell pepper as described in "*Capsicum* Pepper Varieties and Classification (New Mexico State University, Circular 530, College of Agriculture and Home Economics, http://www.reocities.com/wstarron/circ530.pdf).

In yet another embodiment, the length/width ratio of mature pepper fruit of a plant in accordance with the present invention is at most about 4, at most about 3.0, at most about 2.5, at most about 2.0, at most about 1.5.

In yet another embodiment, the width of a mature pepper fruit of a plant in accordance with the present invention is at least about 1.5 cm, at least about 2.0 cm, at least about 3.0 cm, at least about 4.0 cm, at least about 6 cm, at least about 7 cm, at least about 8 cm, at least about 9 cm, at least about 10 cm, or more, at its broadest width.

In yet another embodiment, the width of a mature pepper fruit of a plant in accordance with the present invention is at least 4.0 cm, such as 6.0 cm or more, 7 cm or more, or 8 cm, or more cm, at its broadest width and the length/width ratio is at most 3, preferably at most 2.5, preferably at most 2.0, or at most 1.5.

In yet another embodiment, a pepper plant according to the present invention is a pepper plant representative samples of seeds of which have been deposited under accession numbers NCIMB 41817 or NCIMB 41818; or a pepper plant which is derived from/derivable from/obtained from/obtainable from seed deposit NCIMB 41817 or NCIMB 41818, e.g. a $F_t$-hybrid derived thereof and retaining VE427$^{RB}$-resistance. So, in one aspect the pepper plant according to the present invention comprising VE427$^{RB}$-resistance is obtainable by/obtained by crossing a plant of which seeds were deposited under accession number NCIMB 41817 or NCIMB 41818 with another pepper plant.

In a preferred embodiment, the introgression fragment providing resistance against VE427$^{RB}$ may be a shorter fragment than the fragment found in NCIMB 41817 and/or NCIMB 41818 which still confers a Tsw-resistance breaking TSWV strain-resistance such as Ve427$^{RB}$-resistance. A pepper plant comprising a shorter introgression fragment can be produced by breeding with NCIMB 41817 or NCIMB 41818 and selecting recombinant progeny which retain Ve427$^{RB}$-resistance. For example NCIMB 41817 or NCIMB 41818 may be crossed with a pepper plant lacking the introgression fragment to generate an F1 plant, selfing the F1 to produce an F2 generation (or any further generation) and screening the F2 generation for plants which are Ve427$^{RB}$-resistant using e.g. the resistance assay described herein. A recombinant plant comprising a shorter introgression fragment may then be identified using standard methods, e.g. molecular markers or FISH (Fluorescent in situ hybridization).

Yet another aspect of the present invention refers to fruits of a pepper plant in accordance with the present invention or flesh of such a pepper fruit, i.e., non-propagating parts of a fruit. In one embodiment, pepper fruits of a pepper plant in accordance with the present invention have viable seeds, while in another embodiment the fruits comprise only non-viable seeds or are seedless (parthenocarpic).

One embodiment of the present invention refers to a tissue or a plant cell of a harvested fruit which is not suitable for propagation even under cell tissue culture conditions. Pepper fruits of plants in accordance with the present invention can be selected from a broad range of different types known in the art. For example, pepper fruits may have the following types: Bell (blocky), cayenne, Lamuyo type (long blocky), dulce italiano, conical, capia, sweet charleston, dolma, cherry, jalapeno, shakira, pencil or hot Charleston, Sivri (e.g. Demre Sivri or Kazanli Sivri), Hungarian wax, Kapya/Florinis, banana, Fresno, Serrano, Ancho, Anaheim, Pasilla, Santa Fe, Scotch bonnet, Habanero. Some exemplary but non-limiting pictures of different types of pepper were disclosed in Bosland et al. (1996). The fruits may also be of any color.

Yet another aspect of the present invention refers to seeds of a VE427-resistant plant as described herein or seeds from which a $VE427^{RB}$-resistant plant as described herein can be grown.

A further embodiment relates to the use of a *Capsicum* plant according to the invention as a parent in a cross with another *Capsicum* plant. Also a method generating other *Capsicum* plants comprising $VE427^{RB}$-resistance is provided, i.e. transferring the introgression fragment which confers $VE427^{RB}$-resistance from a plant according to the invention (e.g. from seeds deposited herein or progeny thereof) into other *Capsicum* plants or by transferring a genomic DNA fragment comprising a QTL which confers $VE427^{RB}$-resistance from PA2638 into cultivated *Capsicum* plants.

Yet another aspect refers to plant cells of a plant in accordance with the present invention comprising a genetic element which comprises a $VE427^{RB}$-resistance conferring QTL or a $VE427^{RB}$-resistance conferring part thereof. In one embodiment, such plant cells are regenerable cells, i.e. they can be regenerated into a whole pepper plant which is $VE427^{RB}$-resistant. In another embodiment such cells are non-regenerable. In a further aspect an in vitro cell culture or in vitro tissue culture comprising or consisting of cells of plants of the invention is provided. The cells and tissues may be pollen, ovary, embryo, leaf, stem, hypocotyls, cotyledons, fruit parts, meristem, or other cells/tissues comprising the genetic element conferring $VE427^{RB}$-resistance. Also a regenerated plant is provided.

Resistance of a plant against a Tsw-resistance breaking strain, such as VE427, may be tested by various methods, such as the $VE427^{RB}$-resistance assay disclosed herein. The $VE427^{RB}$-resistance assay described herein is suitable to determine resistance against wild type (WT; P0) and resistance breaking (RB) pathotypes (P1), likewise, i.e. it is not limited to determining resistance against $VE427^{RB}$ and can be used to identify other Tsw-resistance breaking strains and to identify new resistance sources, against other P1 pathotypes. In the different embodiments described herein $VE427^{RB}$ can therefore be replaced by other Tsw-resistance breaking strains which do cause systemic symptoms on *Capsicum* plants comprising the Tsw-gene. It is understood that such embodiments are equally embodiments of the invention.

Resistance Assay

To identify and/or select *Capsicum* plants comprising an introgression fragment which confers $VE427^{RB}$ resistance according to the invention, the following resistance assay, or alternative assays, can be used. The following describes the assay that was used in the Examples and the assay that can determined whether a plant line or variety comprises a $VE427^{RB}$ resistance conferring genetic element according to the invention. The skilled person can equally modify the disclosed assay or develop different assays, e.g. based on field infection with a P1 pathotype (preferably $VE427^{RB}$), based on viliferous insects transmitting P1 or based on different artificial inoculation assays. The assay used should preferably be able to identify *Capsicum* plants comprising a resistance conferring genetic element (e.g. an introgression fragment) through e.g. the (essential) absence of systemic symptoms (or systemic presence of the virus particles) following infection or inoculation of e.g. lower leaves, while susceptible control plants do develop systemic symptoms. Of course, different assays may use a different way of determining whether a plant is resistant or susceptible, but whatever the assay is, if the plants are (re-)tested in the $VE427^{RB}$ resistance assay described herein and they are determined to comprise VE427 resistance according to the present assay, they do comprise a $VE427^{RB}$ resistance conferring genetic element according to the invention.

Preparing of the Pathotype Inoculum

A pathotypes such as P0 or P1, can be/was stored long term as infected *N. benthamiana* leaves or leaf sap in liquid nitrogen.

Before using it for the artificial inoculation test of pepper lines, susceptible plants, such as *N. benthamiana* or *Capsicum* plants not carrying any TSWV resistance genes can be/were infected with the pathotype to check activity of said pathotype (e.g. 5 or more plants can be/were infected). As a negative control, resistant plants can optionally be infected as well (e.g. *Capsicum annuum* plants of deposit NCIMB 41817 and NCIMB 41818 and NCIMB 41936 for P1 and *Capsicum* plants having the Tsw gene for P0).

Activity of the inoculum is confirmed if the susceptible plants develop systemic symptoms. Symptomatic leaves (identified by yellow mottling on the leaves) of these plants can be/were used for the inoculation of the pepper lines to be tested. Electron microscopy can be/was used to exclude the presence of other viruses.

TSWV-Resistance Assay According to the Invention

In a TSWV-resistance assay (such as a $VE427^{RB}$- or P0-resistance assay, or another P1 resistance assay) in accordance with the present invention, a number of plants of a plant line or variety to be tested for resistance against one or more TSWV pathotypes are sown and grown under the same conditions as a number of control plants. Pathotypes are, e.g., P1 ($VE427^{RB}$ of which a representative sample has been deposited at the DSZM under accession number DSM24829) or P0 (wild type TSWV strain, e.g., a TSWV strain against which plants having the Tsw-gene, such as *C. chinense* PI152225, are resistant; such a wild type strain is, e.g., $p105^{WT}$ which can be identified by its S-segment sequence (GenBank Accession No.: DQ376178). In general at least 5 or more, at least 10 or more, at least 12 or more, at least 15 or more, at least 20 or more plants (test plants) per pathotype are sown and grown until they have two cotyledons and five to six true leaves. The growth conditions are e.g., in a glasshouse with sufficient water supply at 26° C./18° C. day/night with a photoperiod of about 14 h. The light source is, e.g., Philips SON-T 400 sodium lamps, photosynthetically active radiation 120 $\mu mol*sec^{-1}*m^{-2}$ µ[PAR]. The growth medium is, e.g., soil such as half turf and half pit. The same conditions were used during the $VE427^{RB}$-resistance assay in the Examples. The skilled person is well-aware of growth conditions for pepper plants. Using the same growth conditions, also control plants were grown. In general, control plants can be divided into two categories: plants which are resistant against a specific pathotype, such as plants which are resistant against pathotypes P0 or P1, and plants which are known to be susceptible to said specific pathotype. The skilled person will understand that preferably both categories of control plants should be part of a resistance assay. In each assay, part of the control plants were treated with a mixture of buffer and the pathotype of interest and part of the control plants were treated with buffer only. Control plants which are inoculated with buffer only should remain symptom free at the end of the assay, i.e. these plants should show neither local nor systemic symptoms of a virus infection.

In general, the two youngest but fully developed leaves of a plant that has two cotyledons and five to six true leaves were mechanically inoculated (e.g. by spraying the inoculum, i.e. a mixture of buffer and pathotype, onto the leaf lamina) for the first time. After, e.g., 5 days, a second mechanical inoculation of the inoculated leaves occurred.

For the inoculation of the two youngest leaves of plants to be tested, infected *N. benthamiana* leaves were frozen in liquid nitrogen, ground to a powder and, e.g., 1 g of leaf powder was mixed with 5 ml of Paul's buffer (Phosphate buffer 0.05 M pH 7, DIECA (Sodium diethyldithiocarbamate trihydrate) 0.005 M, EDTA-$Na_2$ 0.001 M, Sodium thioglycolate 0.005 M). Optionally, the buffer may contain a coloring agent such as active carbon powder to mark inoculated leaves by their darker color caused by active carbon debris compared to non-inoculated leaves. The mixture can be/was, e.g., sprayed on the leaves to be inoculated.

As a negative control, the two youngest but fully developed leaves of a control plant that has two cotyledons and five to six true leaves can/were mechanically inoculated with buffer alone.

A plant was considered resistant if the upper non-inoculated leaves of a plant were essentially without signs of virus—induced symptoms (yellow mottling) 28 days after first inoculation with a specific virus strain, i.e. these plants essentially do not show systemic symptoms. A first observation of symptoms on the inoculated leaf and of systemic symptoms of upper, non-inoculated leaves of test and control plants can be/was assessed for each plant after, e.g. 5, 6 or 7 days. A second observation can be assessed after, e.g., 12, 13 or 14 days. A third observation can be assessed after, e.g., 28, 29, or 30 days. It is noted that the upper non-inoculated leaves are only fully developed by the plant at a later stage than the time point of first inoculation.

In one embodiment, the number of control plants in each category (e.g. susceptible control plants treated with pathotype or treated with buffer only and/or a resistant control plant treated with pathotype or treated with buffer only) is at least 5%, 10%, 25%, 50% compared to the amount of test plants in a resistance assay, however, the number of plants in each category of control plants in a resistance assay is at least 1, preferably at least 5, or at least 10; or the number of control plants is equal to the amount of test plants in an resistance assay. In one embodiment, at least two or more replicates per test are performed. In one embodiment, the amount of tested plants of the same line/variety is at least 5, 6, 10, 12, 15 or 20 test plants per category (test plants treated with pathotype or treated with buffer only).

Analysis

In a VE427$^{RB}$ resistance assay, VE427$^{RB}$ was used as pathotype. Likewise, in a P0 resistance assay, P0, such as p105$^{WT}$ or Ve430$^{WT}$, was used as pathotype.

The test plants can be categorized as "resistant against VE427$^{RB}$" or "resistant against P0", respectively, if (following leaf inoculation with VE427$^{RB}$ or P0, respectively) essentially no systemic symptoms appear on upper, non-inoculated leaves, while in susceptible control plant(s) systemic symptoms appear on the upper, non-inoculated leaves, e.g., under the assay conditions described herein or equivalent assay conditions.

"Systemic symptoms" refers to TSWV symptoms, in particular yellow mottling, which develop leaves that were not inoculated with TSWV, preferably on upper leaves.

"Local symptoms" refers to TSWV symptoms, especially necrotic lesions, which develop on the leaves that were inoculated with TSWV (and optionally marked by, e.g., carbon powder).

"Essentially no systemic symptoms" of plant lines or varieties in an assay as described herein means that the majority of tested plants of a plant line or plant variety, i.e. at least 60% do not show any signs of (virus induced) systemic yellow mottling (chlorosis) on the upper, non-inoculated leaves, while all the susceptible control plants do show systemic symptoms. In one embodiment, at least 70%, 80%, 90%, 91%, 92%, 93%, 94%, 95%, 98% or even 100% of tested plants do not show any signs of (virus induced) systemic yellow mottling (chlorosis) on the upper, non-inoculated leaves.

"Yellow mottling" is the typical symptom of systemic infection of TSWV on pepper which is known to the skilled person. "Yellow mottling" refers to areas of yellow mottle/spot/areas.

"Necrotic lesions" as used herein are small, dark areas where necrosis occurs at inoculated leaves.

Thus, in one embodiment, tested plants showing essentially no systemic symptoms (i.e. no yellow mottling on non-inoculated upper leaves) do essentially show necrotic lesions on the inoculated leaves compared to the control plants which were inoculated with buffer only. This is a local reaction of resistant plants against a pathotype. Plants "essentially showing/developing local necrotic lesions" refers to at least 60%, preferably at least 70%, 80%, more preferably at least 90%, 92%, 93%, 95%, 98%, 99% or 100% showing necrotic lesions on the inoculated leaf e.g. about 28 days after artificial inoculation.

However, the skilled person is aware that the presence/absence of virus in the upper, non-inoculated leaves (compared to the control plants inoculated with buffer only or which are known to be resistant against a specific pathotype, e.g., Ve427) under the herein described resistance assay conditions can also or alternatively be determined by using, e.g. ELISA (Enzyme Linked Immuno-Sorbent Assay) based on the presence (or absence) of a NSs protein of a virus in upper, non-inoculated leaves of plants which were subject of a VE427$^{RB}$-resistance or P0-resistance assay as described herein. Thus, an alternative or additional way to assess the presence/absence of systemic symptoms (and the presence/absence of resistance) is to test whether TSWV virus particles can be found in the upper, non-inoculated leaves.

Production of Ve427$^{RB}$-Resistant *Capsicum* Plants

A *Capsicum* plant, especially cultivated *Capsicum*, comprising Ve427-resistance conferred by an introgression fragment from wild *Capsicum* (e.g. obtainable from PA2638 or other Ve427$^{RB}$-resistant wild *Capsicum* plants) can be generated by a number of methods. In a preferred embodiment, the Capsicums plant is generated by non-transgenic methods, preferably by breeding methods, including one or more method selected from crossing, selfing, backcrossing, double haploid production, embryo rescue, marker assisted breeding, protoplast fusion and the like, or combinations thereof.

The present invention also relates to a method of producing a Ve427 resistant *Capsicum* plant comprising the steps of performing a method for detecting the presence of a quantitative resistance locus (QTL) conferring resistance against Ve427$^{RB}$ in a donor pepper plant according to invention as described above, and transferring a genetic element/nucleic acid sequence comprising at least one QTL, or a Ve427$^{RB}$-resistance-conferring part thereof, from said donor plant to a Ve427$^{RB}$-susceptible recipient *Capsicum* plant. The transfer of said nucleic acid sequence may be performed by any of the methods previously described herein.

In one embodiment the method for identifying a Ve427$^{RB}$-resistant *Capsicum* plant comprises:

a) screening *Capsicum* plants or lines or varieties for Ve427-resistance by performing e.g. a Ve427$^{RB}$-resistance assay as described herein, b) identifying a *Capsicum* plant or line or variety, which does not develop systemic symptoms following Ve427$^{RB}$ infection.

The identified plant line or variety can then be used further, e.g. in a backcrossing scheme or other traditional breeding scheme, to generate a Ve427$^{RB}$-resistant *Capsicum* plant (preferably *C. annuum*), preferably a cultivar or variety having good agronomic properties and comprising the Ve427$^{RB}$-resistance QTL(s).

In one embodiment the method for generating a Ve427-resistant *Capsicum* plant comprises:

a) screening *Capsicum* plants or lines or varieties for Ve427$^{RB}$-resistance by performing e.g. a Ve427$^{RB}$-resistance assay as described herein, b) identifying a *Capsicum* plant or line or variety, which does not develop systemic symptoms following Ve427$^{RB}$ infection, c) crossing said identified plant or line or variety with another *Capsicum* plant, e.g. a plant lacking Ve427$^{RB}$-resistance, to produce an F1 plant, d) selfing and/or crossing (e.g. backcrossing) the F1 plant one or more times, to produce a progeny *Capsicum* plant comprising Ve427$^{RB}$-resistance.

In step a) the *Capsicum* plant line or variety may in one embodiment be a wild *Capsicum* plant, or it may be a cultivated *Capsicum* plant. In one embodiment the plant in step a) is a plant selected from plants deposited under NCIMB 41817, NCIMB 41818 and NCIMB41936, or a progeny thereof, whereby the progeny plant comprises Ve427$^{RB}$-resistance.

In step b) the plant may be identified as comprising Ve427$^{RB}$-resistance if at least 60%, preferably at least 70%, 80%, more preferably at least 90%, 92%, 93%, 95%, 98%, 99% or 100% of Ve427$^{RB}$ infected plants develop no systemic symptoms. In step c) the plant into which the Ve427$^{RB}$-resistance is introduced is preferably a cultivated *Capsicum* plant, preferably an elite breeding line or variety which lacks Ve427$^{RB}$-resistance. Optionally this plant comprises Tsw-resistance, so that the progeny plants developed in step d) comprise both the dominant Tsw resistance gene and the genetic element conferring Ve427$^{RB}$-resistance. A plant comprising Tsw resistance can be identified by e.g. molecular marker analysis and/or in a resistance assay as described herein or any other assay, whereby the *Capsicum* plant is resistant against (i.e. e.g. does not develop systemic symptoms in a TSWV resistance assay as described in the Examples) the wild type TSWV strains (pathotype P0), such as p105WT, or others.

In step d) the presence of the genetic element conferring Ve427$^{RB}$-resistance in the progeny plants can be confirmed, by various methods (such as the Ve427$^{RB}$-resistance assay or similar assay, field trials in areas where Ve427$^{RB}$ strains are found, etc). Optionally also the presence of the Tsw gene can be confirmed by marker and/or TSWV resistance assays.

Another embodiment provides a method for transferring Ve427-resistance from one *Capsicum* plant into another *Capsicum* plant lacking Ve427$^{RB}$-resistance. The method comprises the transfer of the introgression fragment from a Ve427$^{RB}$-resistant donor *Capsicum* plant into a Ve427$^{RB}$-susceptible recipient *Capsicum* plant by crossing said plants. This transfer may thus suitably be accomplished by using traditional breeding techniques. An introgression fragment comprising a Ve427$^{RB}$-resistance-conferring QTL is preferably introgressed into commercial *Capsicum* lines or varieties by using marker-assisted selection (MAS). Marker-assisted breeding or marker-assisted selection involves the use of one or more of the molecular markers for the identification and selection of those offspring plants that contain one or more of the genes that encode for the desired trait. In the present instance, such identification and selection is based on selection of a QTL of the present invention or markers associated therewith or markers associated with the introgression fragment (i.e. markers that are specific for the introgression fragment).

MAS can also be used to develop near-isogenic lines (NIL) harboring the QTL of interest, allowing a more detailed study of each QTL effect and is also an effective method for development of backcross inbred line (BIL) populations. *Capsicum* plants developed according to this embodiment can advantageously derive a majority of their traits from the recipient plant, and derive Ve427$^{RB}$-resistance from the donor plant. As discussed briefly above, traditional breeding techniques can be used to introgress a nucleic acid sequence encoding for Ve427$^{RB}$ resistance into a Ve427$^{RB}$-susceptible recipient *Capsicum* plant. In one method, which is referred to as pedigree breeding, a donor *Capsicum* plant that exhibits resistance to Ve427$^{RB}$ and comprising a nucleic acid sequence encoding for Ve427$^{RB}$-resistance is crossed with a Ve427$^{RB}$ susceptible recipient *Capsicum* plant that preferably exhibits commercially desirable characteristics, such as, but not limited to, disease resistance, insect resistance, valuable fruit characteristics, etc. The resulting plant population (representing the $F_1$ hybrids) is then self-pollinated and sets seeds (F2 seeds). The F2 plants grown from the F2 seeds are then screened for resistance to Ve427$^{RB}$. Alternatively or in addition one or more further generation, such as an F3, F4 or BC1 or BC2 generation, may be screened for Ve427-resistance. The population can be screened, e.g., in accordance with the resistance assay described herein or alternative resistance assays and/or marker-assisted selection can be used, e.g., to confirm the results obtained from the resistance assay and, therefore, several methods may also be used in combination.

Inbred Ve427$^{RB}$-resistant *Capsicum* plant lines can be developed using the techniques of recurrent selection and backcrossing, selfing and/or di-haploids or any other technique used to make parental lines. In a method of recurrent selection and backcrossing, Ve427$^{RB}$-resistance can be introgressed into a target recipient plant (the recurrent parent) by crossing the recurrent parent with a first donor plant, which differs from the recurrent parent and is referred to herein as the “non-recurrent parent”. The recurrent parent is a plant that is non-resistant or has a low level of resistance to Ve427$^{RB}$ (e.g., at least around 60%, at least around 70%, at least around 80% of at least 10 plants in an assay in accordance with the present invention show systemic symptoms after inoculation with Ve427$^{RB}$) and possesses commercially desirable characteristics, such as, but not limited to (additional) disease resistance, insect resistance, valuable fruit characteristics, etc. The non-recurrent parent can be any plant variety or inbred line that is cross-fertile with the recurrent parent. The progeny resulting from a cross between the recurrent parent and non-recurrent parent are backcrossed to the recurrent parent. The resulting plant population is then screened for the desired characteristics, which screening may occur in a number of different ways. For instance, the population can be screened using phenotypic pathology screens such as the resistance assay described herein, quantitative bioassays as known in the art with Ve427$^{RB}$ and/or marker-assisted selection (MAS).

It should be kept in mind that, for instance when introgressing a recessive locus the phenotype conferred by that locus will only be expressed in offspring plants under conditions wherein plants homozygous for the locus are formed.

In general, a method of introducing a desired trait such as Ve427-resistance into a hybrid *Capsicum* variety comprises the steps of:

(a) crossing an inbred *Capsicum* parent with another *Capsicum* plant that comprises one or more desired traits, to produce $F_1$ progeny plants, wherein one desired trait is Ve427$^{RB}$-resistance and selfing the $F_1$ progeny plants one or more times to produce an F2, or F3, or further generation (c) selecting from said F2 or F3 or further generation progeny plants those plants that have the desired trait for example using the TSWV resistance assay as defined herein;

(d) optionally, backcrossing the selected progeny plants with said inbred *Capsicum* parent plant to produce backcross progeny plants;

(e) optionally, selecting for backcross progeny plants that have the desired trait and morphological and physiological characteristics of said inbred *Capsicum* parent plant, wherein said selection for example comprises the resistance assay as described herein;

(f) optionally repeating steps (d) and (e) two or more times in succession to produce selected third or higher backcross progeny plants;

(g) optionally selfing selected backcross progeny in order to identify homozygous plants;

(h) optionally crossing at least one of said backcross progeny or selfed plants with another inbred *Capsicum* parent plant to generate a hybrid *Capsicum* variety with the desired trait and all of the morphological and physiological characteristics of hybrid *Capsicum* variety when grown in the same environmental conditions.

As indicated, the last backcross generation may be selfed in order to provide for pure breeding (inbred) progeny comprising Ve427$^{RB}$-resistance in homozygous form. Thus, the result of recurrent selection, backcrossing and selfing is the production of lines that are genetically homogenous for the genes associated with Ve427$^{RB}$ resistance as well as other genes associated with traits of commercial interest.

The resulting F1 hybrid *Capsicum* plant may either comprise the genetic element conferring Ve427$^{RB}$-resistance in homozygous or in heterozygous form. Thus, the in one embodiment two inbred parent lines are provided, each having good agronomic characteristics and each comprising the genetic element conferring Ve427$^{RB}$-resistance in homozygous form, so that the F1 hybrid comprises the genetic element conferring Ve427$^{RB}$-resistance in homozygous form. In another embodiment two inbred parent lines are provided, each having good agronomic characteristics but only one the inbred parent lines comprising the genetic element conferring Ve427$^{RB}$-resistance in homozygous form while the other one lacks the genetic element conferring Ve427$^{RB}$-resistance, so that the F1 hybrid comprises the genetic element conferring Ve427$^{RB}$-resistance in heterozygous form. Preferably, inbred parent lines (and F1 hybrids) are of the species *Capsicum annuum* L. and produce good quality pepper fruits. In one embodiment the pepper fruits are bell peppers, but any other fruit shape/type and any color may be provided.

Thus, the use of a *Capsicum* plant, preferably a *Capsicum annuum* plant, as a parent in F1 hybrid pepper production, wherein said F1 hybrid parent comprises a genetic element conferring Ve427$^{RB}$-resistance. In one embodiment the genetic element is obtainable from seeds deposited under accession numbers selected from NCIMB 41817, NCIMB 41818 and NCIMB41936, or a progeny thereof, whereby the progeny plant comprises Ve427$^{RB}$-resistance.

Seeds of any of the plants described herein are also provided, especially seeds from which F1 hybrids described herein above can be grown and/or seeds from which an inbred *C. annuum* comprising Ve427$^{RB}$-resistance can be grown, whereby the resistance is the resistance as found in seeds deposited under Accession number NCIMB 41817, NCIMB 41818 and/or NCIMB41936; i.e. wherein the Ve427-resistance is obtainable from/can be obtained from said seeds.

The goal of plant breeding is to combine in a single variety various desirable traits. For commercial crops, these traits may include resistance to diseases and insects, tolerance to heat and drought, reducing the time to crop maturity, greater yield, and better agronomic quality, fruit uniformity, etc. Uniformity of plant characteristics such as germination and stand establishment, growth rate, maturity, and plant height may also be of importance.

Commercial crops are bred through techniques that take advantage of the plant's method of pollination. A plant is self-pollinated if pollen from one flower is transferred to the same or another flower of the same plant. A plant is sib pollinated when individuals within the same family or line are used for pollination. A plant is cross-pollinated if the pollen comes from a flower on a different plant from a different family or line. Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

The development of a hybrid pepper variety in a *Capsicum* plant breeding program involves three steps: (1) the selection of plants from various germplasm pools for initial breeding crosses; (2) the selfing of the selected plants from the breeding crosses for several generations to produce a series of inbred lines, which, individually breed true and are highly uniform; and (3) crossing a selected inbred line with an unrelated inbred line to produce the hybrid progeny ($F_1$). After a sufficient amount of inbreeding successive filial generations will merely serve to increase seed of the developed inbred. Preferably, an inbred line should comprise homozygous alleles at about 95% or more of its loci.

An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid *Capsicum* plants can then be generated from this hybrid seed supply.

An aspect of the present invention refers to a Ve427-resistant pepper plant, or a part thereof, obtainable by a method of the invention. Another aspect of the present invention relates to a Ve427$^{RB}$-resistant *Capsicum* plant, or part thereof, comprising the QTL conferring Ve427-resistance wherein said QTL is not in its natural genetic background. The Ve427$^{RB}$-resistant pepper plants of the present invention can be of any genetic type such as inbred, hybrid, haploid, dihaploid or transgenic. Further, the plants of the present invention may be heterozygous or homozygous for the Ve427$^{RB}$ resistance trait, preferably homozygous. Although the QTLs of the present invention, as well as resistance-conferring parts thereof, may be transferred to any *Capsicum* plant in order to provide for a Ve427$^{RB}$-resistant *Capsicum* plant, the methods and plants of the invention are preferably related to plants of the species *Capsicum annuum*. The Ve427$^{RB}$-resistant inbred *Capsicum* lines described herein can be used in additional crossings to create Ve427$^{RB}$-resistant hybrid plants. For example, a first Ve427$^{RB}$-resistant inbred *Capsicum* plant of the invention can be crossed with a second inbred *Capsicum* plant possessing commercially desirable traits such as, but not limited to, disease resistance, insect resistance, desirable fruit characteristics, desired fruit shape and fruit size, etc. This second inbred *Capsicum* line may or may not be Ve427$^{RB}$-resistant. Preferably, this second inbred *Capsicum* line is Ve427$^{RB}$-resistant.

Another aspect of the present invention relates to a method of producing seeds that can be grown into Ve427$^{RB}$-resistant pepper plants. In one embodiment, the method comprises the steps of providing a Ve427$^{RB}$-resistant *Capsicum* plant of the invention, crossing said Ve427$^{RB}$-resistant plant with another *Capsicum* plant, and collecting seeds resulting from said cross, which when planted, produce Ve427$^{RB}$-resistant *Capsicum* plants. Alternatively, the method comprises the steps of providing a Ve427$^{RB}$-resistant *Capsicum* plant of the invention and selfing the plant, and collecting seeds resulting from said selfing.

In another embodiment, the method comprises the steps of providing a Ve427-resistant *Capsicum* plant of the invention, crossing said Ve427$^{RB}$-resistant plant with a *Capsicum* plant, collecting seeds resulting from said cross, growing said seeds into plants, selecting Ve427$^{RB}$-resistant plants by any of the methods described herein, self-pollinating the selected plants for a sufficient number of generations to obtain plants that are fixed for an allele that confers Ve427-resistance in the plants, backcrossing the plants thus produced with *Capsicum* plants having desirable phenotypic traits for a sufficient number of generations to obtain *Capsicum* plants that are Ve427$^{RB}$-resistant and have desirable phenotypic traits, and collecting the seeds produced from the plants resulting from the last backcross, which when planted, produce *Capsicum* plants which are Ve427-resistant.

In an alternative embodiment for producing a Ve427-resistant *Capsicum* plant, protoplast fusion can be used for the transfer of nucleic acids from a donor *Capsicum* plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot interbreed in nature, is cultured in vitro and is regenerated into a hybrid plant exhibiting the desirable combination of traits. More specifically, a first protoplast can be obtained from a *Capsicum* plant or other plant line that exhibits resistance to infection by Ve427$^{RB}$. A second protoplast can be obtained from a second *Capsicum* or other plant line, preferably a *Capsicum* line that comprises commercially valuable characteristics, such as, but not limited to disease resistance, insect resistance, valuable fruit characteristics, etc. The protoplasts are then fused using traditional protoplast fusion procedures, which are known in the art.

Alternatively, embryo rescue may be employed in the transfer of a nucleic acid comprising the QTL of the present invention or a Ve427$^{RB}$-resistance-conferring part thereof from a donor plant to a recipient plant. Embryo rescue can be used as a procedure to isolate embryo's from crosses wherein plants fail to produce viable seed. In this process, the fertilized ovary or immature seed of a plant is cultured in vitro and regenerated to create a new plant.

Further, isolated cells, in vitro cell cultures and tissue cultures, protoplast cultures, plant parts, harvested material (e.g. harvested pepper fruits), pollen, ovaries, flowers, seeds, stamen, flower parts, etc. comprising in each cell a genetic element conferring Ve427$^{RB}$-resistance are provided. Thus, when said cells or tissues are regenerated or grown into a whole *Capsicum* plant, the plant comprises Ve427$^{RB}$-resistance.

Thus, also an in vitro cell culture and/or tissue culture of cells or tissues of plants of the invention is provided. The cell or tissue culture can be treated with shooting and/or rooting media to regenerate a *Capsicum* plant.

Also vegetative or clonal propagation of plants according to the invention is encompassed herein. Many different vegetative propagation techniques exist. Cuttings (nodes, shoot tips, stems, etc.) can for example be used for in vitro culture as described above. Also other vegetative propagation techniques exist and can be sued, such as grafting, or air layering. In air layering a piece of stem is allowed to develop roots while it is still attached to the parent plant and once enough roots have developed the clonal plant is separated from the parent.

Thus, in one aspect a method is provided comprising:

a) Obtaining a part of a plant of the invention (e.g. cells or tissues, e.g. cuttings), b) Vegetatively propagating said plant part to generate an identical plant from the plant part.

Thus, also the use of vegetative plant parts of plants of the invention for clonal/vegetative propagation is an embodiment of the invention.

Also a plurality of harvested pepper fruits comprising a genetic element conferring Ve427$^{RB}$-resistance are provided, as are food or feed products comprising parts of such pepper fruits.

In one aspect, the fruits are seedless fruits.

Deposit Information

A representative sample of the Tsw-resistance breaking TSWV strain Ve427 was deposited by Nunhems B.V. at the DSMZ (Deutsche Sammlung von Mikroorganismen and Zellkulturen GmbH, Inhoffenstr. 7B, 38124 Braunschweig, Germany) on Apr. 19, 2011, under accession number DSM24829.

A representative sample of *Capsicum annuum* seeds comprising the Ve427$^{RB}$ resistance gene introgression were deposited by Nunhems B.V. at the NCIMB (NCIMB Limited, Ferguson Building, Craibstone Estate, Bucksburn, Aberdeen, AB21 9YA Scotland, UK) on Mar. 14, 2011 tinder Accession numbers NCIMB 41817 and NCIMB 41818.

A representative sample of PA2638 was deposited by Nunhems B.V. at the NCIMB (NCIMB Limited, Ferguson Building, Craibstone Estate, Bucksburn, Aberdeen, AB21 9YA Scotland, UK) on Feb. 23, 2012 under Accession number NCIMB41936.

The Applicant requests that samples of the biological material and any material derived therefrom be only released to a designated Expert in accordance with Rule 32(1) EPC or related legislation of countries or treaties having similar rules and regulation, until the mention of the grant of the patent, or for 20 years from the date of filing if the application is refused, withdrawn or deemed to be withdrawn.

Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The following non-limiting examples illustrate the production of pepper plants, seeds and fruits according to the invention. All references mentioned herein are incorporated by reference.

EXAMPLES

Identification of Resistance Sources Effective Against Ve427$^{RB}$

Resistance screening was done under natural infection conditions in Almeria, Spain, where the resistance-breaking strain Ve427$^{RB}$ and its corresponding wild type Ve430$^{WT}$ have originally been isolated from (Margaria et al. (Plant Pathology Vol 53: p794)). Surprisingly, wild accession PA2638 showed resistance against resistance-breaking strain Ve427$^{RB}$.

Resistance against resistance-breaking strain Ve427$^{RB}$ was confirmed by using artificial inoculation with isolated Tsw-resistance breaking strain Ve427$^{RB}$ in Turin, Italy.

Inoculation method and resistance assessment was carried out as described in above and further below. Exemplary pictures of local and systemic symptoms can be found, e.g., in Margaria et al. (2007, MPMI Vol 20: 547-558).

Resistance-breaking strain Ve427$^{RB}$ and wild type (WT) strain p105$^{WT}$ were evaluated for symptom development on a set of host species. Twelve plants per genotype were either inoculated with Ve427$^{RB}$ or with the wild type strain. Post inoculation, local symptoms were evaluated in inoculated leaves after 7, 15 and 28 days and systemic symptoms were evaluated in non-inoculated, upper leaves after 15 and 28 days.

The plants to be tested and control plants were sown and grown under the same conditions until they have two cotyledons and five to six true leaves. The growth conditions were: glasshouse, sufficient water supply, temperature: around 26° C./18° C. day/night with a photoperiod of about 14 h, light intensity: around 120 μmol*sec$^{-1}$*m$^{-2}$ μ[PAR], growth medium: soil (half turf and half pit).

The two youngest but fully developed leaves of a plant that has two cotyledons and five to six true leaves were mechanically inoculated by spraying a mixture of buffer with active carbon powder and Ve427RB on the leaves. After 5 days, a second mechanical inoculation occurred. For inoculation, 1 g of leave powder of infected *N benthamiana* leaves was mixed with 5 ml of Paul's buffer (Phosphate buffer 0.05 M pH 7, DIECA (Sodium dicthyldithiocarbamatc trihydratc) 0.005 M, EDTA-Na2 0.001 M, Sodium thioglycolate 0.005 M). Leaves to be inoculated were sprayed until they were moist on the upper surface. The skilled person will understand that the amount of buffer depends on the surface to be covered. Thus, e.g., around 0.1 ml, around 0.2 ml, around 0.5 ml, around 0.7 ml, around 1.0 ml, around 1.5 ml, around 2.0 ml, around 2.5 ml, around 4.0 ml of buffer may be used to moisturize the upper surface of a leaf.

Activity of each pathotype was confirmed by inoculating leaves of susceptible *N. benthamiana* plants. All inoculated *N. benthamiana* plants showed systemic symptoms after 28 days. As a negative control, the two youngest but fully developed leaves of plants that have two cotyledons and five to six true leaves can/were mechanically inoculated with buffer alone. No systemic (or local) symptoms were detected after 28 days.

Control Variety *C. chinensis* PI152225 (designated CV1) which carries the Tsw gene and is resistant against the wild type p105$^{WT}$ (and susceptible against Ve427$^{RB}$) and Control Variety Quadrato D'Asti (commercially available, see e.g., http://www.macrolibrarsi.it/prodotti/_peperone-quadrato-d-asti-5-gr-b525.php) (designated CV2) which does not carry the Tsw gene (and is, thus, susceptible against p105$^{WT}$ and is susceptible against Ve427) were used as control lines. However, also other control lines can be used which are known/can be identified to be, e.g. resistant/susceptible against wild type TSWV. Results are shown in Table 1 below. Pathotype P0 (p105$^{WT}$) inocluated plants, CV2 and PA2638 showed systemic symptoms 28 days post first inoculation, while CV1 plants (comprising the Tsw resistance gene) did not show systemic symptoms And were therefore, as expected, resistant against the wild type strain.

In contrast, pathotype P1 (Ve427) inoculated plants of CV1 showed systemic symptoms, confirming that Tsw is not effective against P1. PA2638, however, did not show systemic symptoms. This wild accession is, therefore, indeed resistant against P1 and the local necrotic reaction at the inoculation site seems to prevent systemic virus spread.

TABLE 1

Phenotypes after artificial inoculations 28 days after inoculation as described in the section resistance assay above

| | P0 (p105$^{WT}$) | P1 (Ve427$^{RB}$) |
|---|---|---|
| CV2 (susceptible against WT and Ve427$^{RB}$) | Local and systemic yellow mottling<br>No necrotic lesions on inoculated leaves. | Local and systemic yellow mottling<br>No necrotic lesions on inoculated leaves. |
| CV1 (resistant against WT strains, susceptible against Ve427$^{RB}$) | No yellow mottling on non-inoculated leaves<br>Necrotic lesions on inoculated leaves | Local and systemic yellow mottling<br>No necrotic lesions on inoculated leaves |
| PA2638 (susceptible against WT strain, resistant against Ve427$^{RB}$) | Local and systemic yellow mottling.<br>No necrotic lesions on inoculated leaves. | No yellow mottling on non-inoculated leaves<br>Necrotic lesions on inoculated leaf |
| Control (buffer only) | No yellow mottling on leaves<br>No necrotic lesions on inoculated leaves. | No yellow mottling on leaves<br>No necrotic lesions on inoculated leaves. |

Example 2

Introgression of Resistance Against P1 (Ve427) into Elite Pepper Breeding Lines In order to effectively control TSWV pathotypes P0 and P1, a backcross program was started using an elite pepper breeding line comprising the dominant Tsw gene, so that PA2638 derived resistance and Tsw-gene conferred resistances are stacked.

Wild accession PA2638 was crossed with parent lines belonging to the Blocky Bell type (*Capsicum annuum* L.) and carrying the Tsw gene derives from *C. chinense* PI152225. $F_1$ progeny were selfed for at least two times.

Marker analysis using published molecular markers for Tsw confirmed that PA2638 does not contain the dominant Tsw gene, while the elite Blocky Bell pepper breeding line does contain the Tsw gene.

Progeny lines comprising introgression fragments from PA2638 were tested for systemic symptom development following Ve427[RB] inoculations as described in Example 1, results of which are shown in Table 2. Twelve plants per line were tested. Systemic symptoms (yellow mottling on upper, non-inoculated leaves) were assessed 28 days after first inoculation.

TABLE 2

Ve427[RB] resistance assay results of different lines after 28 days post first inoculation.

| | Ve427[RB] | |
|---|---|---|
| | Plants without systemic symptoms [%] | % systemic symptoms (yellow mottlings) |
| CV1 | 0% | 100% |
| PA2638 | 92% | 8% |
| NCIMB 41817 | 92% | 8% |
| NCIMB 41818 | 92% | 8% |
| CV2 | 0% | 100% |

Pepper plants with essentially the same level of resistance against the Tsw-resistance breaking strain Ve427[RB] (comprise a resistance-conferring introgression fragment from wild *Capsicum* accession PA2638 in their genome) were selected. Seeds of these lines were deposited under accession numbers NCIMB 41817 and NCIMB 41818. Seeds of the wild *Capsicum* PA2638 were deposited under accession number NCIMB 41936.

The invention claimed is:

1. A cultivated pepper plant of the species *Capsicum annuum*, which is resistant against the Tsw-resistance breaking strain of Tomato Spotted Wilt Virus (TSWV) designated Ve427$^{RB}$, a representative sample of said strain having been deposited under accession number DSM 24829; wherein said pepper plant comprises a genetic element from wild pepper accession PA2638, representative seeds of said accession having been deposited under accession number NCIMB 41936, wherein said genetic element comprises a Ve427$^{RB}$-resistance conferring QTL; and wherein said cultivated pepper plant is of a line whereof at least 60% of the plants infected with or inoculated with Ve427$^{RB}$ develop no systemic symptoms.

2. The pepper plant according to claim 1, wherein said plant is obtainable by crossing a plant of wild accession PA2638, representative seeds thereof having been deposited under accession number NCIMB 41936; or by crossing a *Capsicum annuum* plant of which seeds were deposited under accession numbers NCIMB 41817 or NCIMB 41818; with another *Capsicum annuum* plant.

3. The pepper plant according to claim 1, wherein said pepper plant produces fruits of blocky bell type, Cayenne type, Lamuyo, Dulce Italiano, Conical, Capia, Sweet Charleston, Dolma, Cherry, Jalapeno type, Shakira, Pencil or Hot Charleston, Sivri, Hungarian Wax, Kapya, banana, ancho, Fresno, Serrano, Anaheim, Pasilla, Santa Fe, Scotch bonnet, or Habanero.

4. The pepper plant according to claim 1, wherein said pepper plant is an inbred line or an $F_1$ hybrid.

5. The pepper plant according to claim 1, comprising the QTL in its genome, and further comprising the dominant Tsw gene from *Capsicum chinense* in its genome.

6. The pepper plant according to claim 5, wherein the plant shows no systemic symptoms after infection with or inoculation with a wild type TSWV strain.

7. The pepper plant according to claim 5, wherein the presence of the QTL is detectable by using a DNA marker.

8. The pepper plant according to claim 1, which comprises the QTL and which comprises resistance against $Ve427^{RB}$, a representative sample of which has been deposited under accession number DSM 24829, wherein said pepper plant is of a line whereof at least 60% of plants tested in a $Ve427^{RB}$-resistance assay show no systemic symptoms on upper, non-inoculated leaves after about 28 days post first inoculation with strain $Ve427^{RB}$.

9. The pepper plant according to claim 1, wherein the QTL is obtainable by crossing a plant, of which seeds were deposited under Accession number NCIMB 41817, NCIMB 41818 or NCIMB 41936, with another *Capsicum annuum* plant.

10. Seeds from which a pepper plant according to claim 1 can be grown.

11. Fruits or parts thereof, of a pepper plant according to claim 1, wherein said parts comprise the QTL.

12. The fruits according to claim 11, wherein said fruits are at least 7 cm long and/or at least 2 cm wide.

13. The fruits according to claim 11, wherein the fruit is a sweet pepper fruit.

14. An in vitro cell or tissue culture of a pepper plant according to claim 1.

15. A pepper plant of the species *Capsicum annuum*, which is resistant against the Tsw-resistance breaking strain of Tomato Spotted Wilt Virus (TSWV) designated $Ve427^{RB}$, obtained by crossing a pepper plant of claim 1 with another *Capsicum annuum* plant.

16. The pepper plant according to claim 15, wherein at least 60% of plants infected with or inoculated with $Ve427^{RB}$ develop no systemic symptoms.

17. The pepper plant according to claim 3, wherein the fruits produced are of the blocky bell type or Lamuyo type.

18. The pepper plant according to claim 6, wherein the wild type TSWV strain is $Br01^{WT}$, $p105^{WT}$, $Ve430^{WT}$, $Br20^{WT}$ or $p170^{WT}$.

19. A method for producing a *Capsicum annuum* plant which is resistant to a Tomato Spotted Wilt Virus (TSWV) strain designated $Ve427^{RB}$ comprising:

a) crossing a *Capsicum annuum* plant of claim 1 with another *Capsicum annuum* plant to produce an F1 plant, and b) selfing and/or crossing the F1 plant one or more times to produce a progeny *Capsicum annuum* plant comprising $Ve427^{RB}$ resistance.

* * * * *

SEQUENCE LISTING

```
<160> NUMBER OF SEQ ID NOS: 2

<210> SEQ ID NO 1
<211> LENGTH: 468
<212> TYPE: PRT
<213> ORGANISM: Tomato Spotted Wilt Virus

<400> SEQUENCE: 1

Met Met Ser Ser Ser Val Tyr Glu Ser Ile Ile Gln Thr Arg Ala Ser
1               5                   10                  15

Val Trp Gly Ser Thr Ala Ser Gly Lys Ala Val Val Asp Ser Tyr Trp
            20                  25                  30

Ile His Glu Leu Gly Thr Gly Ser Gln Leu Val Gln Thr Gln Leu Tyr
        35                  40                  45

Ser Asp Ser Arg Ser Lys Ser Ser Phe Gly Tyr Thr Ala Lys Val Gly
    50                  55                  60

Asp Leu Pro Cys Glu Glu Glu Glu Ile Leu Ser Gln His Val Tyr Ile
65                  70                  75                  80

Pro Ile Phe Asp Asp Ile Asp Phe Ser Ile Asn Ile Asp Asp Ser Val
                85                  90                  95

Leu Ala Leu Ser Val Cys Ser Asn Thr Val Asn Ala Asn Gly Val Lys
            100                 105                 110

His Gln Gly His Leu Lys Val Leu Ser Pro Ala Gln Leu His Ser Ile
        115                 120                 125

Gly Ser Ile Met Asn Arg Ser Asp Ile Thr Asp Arg Phe Gln Leu Gln
    130                 135                 140

Glu Lys Asp Ile Ile Pro Asn Asp Arg Tyr Ile Glu Ala Ala Asn Lys
145                 150                 155                 160

Gly Ser Leu Ser Cys Val Lys Glu His Thr Tyr Lys Ile Glu Met Cys
                165                 170                 175

Tyr Asn Gln Ala Leu Gly Lys Val Asn Val Leu Ser Pro Asn Arg Asn
            180                 185                 190

Val His Glu Trp Leu Tyr Ser Phe Lys Pro Asn Phe Asn Gln Val Glu
        195                 200                 205

Ser Asn Asn Arg Thr Val Asn Ser Leu Ala Val Lys Ser Leu Leu Met
    210                 215                 220

Ser Ala Glu Asn Asn Ile Met Pro Asn Ser Gln Ala Phe Val Lys Ala
225                 230                 235                 240
```

-continued

```
Ser Thr Asp Ser His Phe Lys Leu Ser Leu Trp Leu Arg Val Pro Lys
                245                 250                 255

Val Leu Lys Gln Ile Ser Ile Gln Lys Leu Phe Lys Val Ala Gly Asp
            260                 265                 270

Glu Thr Asn Lys Thr Phe Tyr Leu Ser Ile Ala Cys Ile Pro Asn His
        275                 280                 285

Asn Ser Val Glu Thr Ala Leu Asn Ile Thr Val Ile Cys Lys His Gln
    290                 295                 300

Leu Pro Ile Arg Lys Cys Lys Ala Pro Phe Glu Leu Ser Met Met Phe
305                 310                 315                 320

Ser Asp Leu Lys Glu Pro Tyr Asn Ile Val His Asp Pro Ser Tyr Pro
                325                 330                 335

Gln Arg Ile Val His Ala Leu Leu Glu Thr His Thr Ser Phe Ala Gln
            340                 345                 350

Val Leu Cys Asn Asn Leu Gln Glu Asp Val Ile Ile Tyr Thr Leu Asn
        355                 360                 365

Asn His Glu Leu Thr Ser Gly Lys Leu Asp Leu Gly Glu Arg Thr Leu
    370                 375                 380

Asn Tyr Ser Glu Asp Ala Tyr Lys Arg Lys Tyr Phe Leu Ser Lys Thr
385                 390                 395                 400

Leu Glu Cys Leu Pro Ser Asn Thr Gln Thr Met Ser Tyr Leu Asp Ser
                405                 410                 415

Ile Gln Ile Pro Ser Trp Lys Ile Asp Phe Ala Arg Gly Glu Ile Lys
            420                 425                 430

Ile Ser Pro Gln Ser Ile Ser Val Ala Lys Ser Leu Leu Lys Leu Asp
        435                 440                 445

Leu Ser Gly Ile Lys Lys Lys Glu Ser Lys Ile Lys Glu Ala Tyr Ala
    450                 455                 460

Ser Gly Ser Lys
465


<210> SEQ ID NO 2
<211> LENGTH: 468
<212> TYPE: PRT
<213> ORGANISM: Artificial Sequence
<220> FEATURE:
<223> OTHER INFORMATION: NSs protein of Tsw-resistance breaking strain
      VEW427RB

<400> SEQUENCE: 2

Met Met Ser Ser Ser Val Tyr Glu Ser Ile Ile Gln Thr Arg Ala Ser
1               5                   10                  15

Val Trp Gly Ser Thr Ala Ser Gly Lys Ala Val Val Asp Ser Tyr Trp
            20                  25                  30

Ile His Glu Leu Gly Thr Gly Ser Gln Leu Val Gln Thr Gln Leu Tyr
        35                  40                  45

Ser Asp Ser Arg Ser Lys Ser Ser Phe Gly Tyr Thr Ala Lys Val Gly
    50                  55                  60

Asp Leu Pro Cys Glu Glu Glu Glu Ile Leu Ser Gln His Val Tyr Ile
65                  70                  75                  80

Pro Ile Phe Asp Asn Ile Asp Phe Ser Ile Asn Ile Asp Asp Ser Val
                85                  90                  95

Leu Ala Leu Ser Val Cys Ser Asn Thr Val Asn Ala Asn Gly Val Lys
            100                 105                 110

His Gln Gly His Leu Lys Val Leu Ser Pro Ala Gln Leu His Ser Ile
        115                 120                 125
```

-continued

```
Gly Ser Ile Met Asn Arg Ser Asp Ile Thr Asp Arg Phe Gln Leu Gln
    130                 135                 140

Glu Lys Asp Ile Ile Pro Asn Asp Arg Tyr Ile Glu Ala Ala Asn Lys
145                 150                 155                 160

Gly Ser Leu Ser Cys Val Lys Glu His Thr Tyr Lys Ile Glu Met Cys
                165                 170                 175

Tyr Asn Gln Ala Leu Gly Lys Val Asn Val Leu Ser Pro Asn Arg Asn
            180                 185                 190

Val His Glu Trp Leu Tyr Ser Phe Lys Pro Asn Phe Asn Gln Val Glu
        195                 200                 205

Ser Asn Asn Arg Thr Val Asn Ser Leu Ala Val Lys Ser Leu Leu Met
    210                 215                 220

Ser Ala Glu Asn Asn Ile Met Pro Asn Ser Gln Ala Phe Val Lys Ala
225                 230                 235                 240

Ser Thr Asp Ser His Phe Lys Leu Ser Leu Trp Leu Arg Val Pro Lys
                245                 250                 255

Val Leu Lys Gln Ile Ser Ile Gln Lys Leu Phe Lys Val Ala Gly Asp
            260                 265                 270

Glu Thr Asn Lys Thr Phe Tyr Leu Ser Ile Ala Cys Ile Pro Asn His
        275                 280                 285

Asn Ser Val Glu Thr Ala Leu Asn Ile Thr Val Ile Cys Lys His Gln
    290                 295                 300

Leu Pro Ile Arg Lys Cys Lys Ala Pro Phe Glu Leu Ser Met Met Phe
305                 310                 315                 320

Ser Asp Leu Lys Glu Pro Tyr Asn Ile Val His Asp Pro Ser Tyr Pro
                325                 330                 335

Gln Arg Ile Val His Ala Leu Leu Glu Thr His Thr Ser Phe Ala Gln
            340                 345                 350

Val Leu Cys Asn Asn Leu Gln Glu Asp Val Ile Ile Tyr Thr Leu Asn
        355                 360                 365

Asn His Glu Leu Thr Ser Gly Lys Leu Asp Leu Gly Glu Arg Thr Leu
    370                 375                 380

Asn Tyr Ser Glu Asp Ala Tyr Lys Arg Lys Tyr Phe Leu Ser Lys Thr
385                 390                 395                 400

Leu Glu Cys Leu Pro Ser Asn Ile Gln Thr Met Ser Tyr Leu Asp Ser
                405                 410                 415

Ile Gln Ile Pro Ser Trp Lys Ile Asp Phe Ala Arg Gly Glu Ile Lys
            420                 425                 430

Ile Ser Pro Gln Ser Ile Ser Val Ala Lys Ser Leu Leu Lys Leu Asp
        435                 440                 445

Leu Ser Gly Ile Lys Lys Lys Glu Ser Lys Ile Lys Glu Ala Tyr Ala
    450                 455                 460

Ser Gly Ser Lys
465
```